US012589004B2

(12) United States Patent
Hawkes et al.

(10) Patent No.: US 12,589,004 B2
(45) Date of Patent: Mar. 31, 2026

(54) SYSTEMS AND METHODS FOR PATIENT-SPECIFIC TOTAL DISC REPLACEMENT

(71) Applicant: Nexus TDR, Inc., Salt Lake City, UT (US)

(72) Inventors: David T. Hawkes, Pleasant Grove, UT (US); Peter Halverson, Draper, UT (US)

(73) Assignee: Nexus TDR, Inc., Salt Lake City, UT (US)

( * ) Notice: Subject to any disclaimer, the term of this patent is extended or adjusted under 35 U.S.C. 154(b) by 921 days.

(21) Appl. No.: 15/423,582

(22) Filed: Feb. 2, 2017

(65) Prior Publication Data

US 2017/0216047 A1 Aug. 3, 2017

Related U.S. Application Data

(60) Provisional application No. 62/290,385, filed on Feb. 2, 2016.

(51) Int. Cl.
*A61F 2/44* (2006.01)
*A61F 2/30* (2006.01)

(52) U.S. Cl.
CPC ........ *A61F 2/4425* (2013.01); *A61F 2/30942* (2013.01); *A61F 2002/30179* (2013.01); *A61F 2002/30232* (2013.01); *A61F 2002/30462* (2013.01); *A61F 2002/30639* (2013.01); *A61F 2002/3096* (2013.01); *A61F 2002/443* (2013.01)

(58) Field of Classification Search
CPC .................................................. A61F 2/4425
See application file for complete search history.

(56) References Cited

U.S. PATENT DOCUMENTS

| | | | |
|---|---|---|---|
| 4,267,608 A | 5/1981 | Bora, Jr. | |
| 6,159,168 A * | 12/2000 | Warner | A61B 5/1107 |
| | | | 600/594 |
| 7,606,613 B2 * | 10/2009 | Simon | A61B 34/20 |
| | | | 600/426 |

(Continued)

FOREIGN PATENT DOCUMENTS

| | | |
|---|---|---|
| AU | 2017214484 B2 | 2/2017 |
| EP | 3410988 A1 | 12/2018 |

(Continued)

OTHER PUBLICATIONS

International Search Report from related International PCT Application No. PCT/US17/16308, May 9, 2017.

(Continued)

*Primary Examiner* — Andrew Yang
(74) *Attorney, Agent, or Firm* — Bryant Keller; Kirton McConkie; John Oldroyd

(57) ABSTRACT

A method of tailoring a spinal implant to correspond to a specific patient's needs includes: pre-operatively evaluating a patient to determine a desired spinal segment response; and modifying one or more features of flexures of an implant to provide the desired spinal segment response. Modifying one or more features of flexures of the implant can include modifying one or more of a thickness, width, length and/or shape of the features of the flexures. Various systems for executing the methodologies taught herein are also provided.

22 Claims, 23 Drawing Sheets

(56)                       References Cited

U.S. PATENT DOCUMENTS

| | | | | |
|---|---|---|---|---|
| 8,308,801 | B2 | 11/2012 | Halverson | |
| 8,721,724 | B2 * | 5/2014 | Lechmann | ............ A61F 2/4425 |
| | | | | 623/17.16 |
| 9,314,346 | B2 | 4/2016 | Halverson | |
| 2006/0282020 | A1 | 12/2006 | Bertagnoli | |
| 2006/0293752 | A1 | 12/2006 | Moumene | |
| 2008/0195213 | A1 | 8/2008 | Halverson | |
| 2010/0241232 | A1 * | 9/2010 | Halverson | ............ A61F 2/4425 |
| | | | | 623/17.16 |

FOREIGN PATENT DOCUMENTS

| | | | |
|---|---|---|---|
| WO | 2002039889 | A2 | 5/2002 |
| WO | 2004041131 | A2 | 5/2004 |
| WO | 2010108010 | A2 | 9/2010 |
| WO | 2011104028 | A1 | 9/2011 |

OTHER PUBLICATIONS

Examination Report from related Australian Patent Application No. 2017214484, Feb. 2, 2016.

* cited by examiner

Anterior ◄─────┼─────► Posterior

1. Establish ROM from Xray (Assume final load*)

2. Establish HFZ Loading Knee
(% of Direction ROM, load* (Yellow Dots))

4. Establish HFZ Stiffness between dots

5.Finish up with a sigmoidal curve
(Boltzman, DIP Boltzman, FreeHand)

6. In vitro we can compare our results

SYSTEMS AND METHODS FOR PATIENT-SPECIFIC TOTAL DISC REPLACEMENT

CROSS-REFERENCE TO RELATED APPLICATIONS

This application claims the benefit of U.S. Provisional Application No. 62/290,385 filed Feb. 2, 2016.

This application is related to prior application Ser. No. 12/726,816, filed Mar. 18, 2010, now U.S. Pat. No. 9,314, 346, and to prior application Ser. No. 12/029,046 filed Feb. 11, 2008, now U.S. Pat. No. 8,308,801, both of which applications are incorporated herein by reference.

BACKGROUND OF THE INVENTION

1. Field of the Invention

The present invention relates generally to treatment of degeneration of spinal joints.

2. Background and Related Art

The human spine functions through a complex interaction of several parts of the anatomy. FIGS. 1 and 2 (FIG. 2 being the cross-section A-A of FIG. 1) illustrate a segment of the spine 4, with vertebra 5. The vertebra 5 includes the vertebral body 6, the spinous process 8, transverse process 10, pedicle 12, and laminae 14. A functional spine, comprising several vertebra 5, typically subcategorized as being part of the cervical, thoracic, lumbar, sacral, and coccygeal regions as known, provides support to the head, neck, trunk, transfers weight to lower limbs, protects the spinal cord 20, from which peripheral nerves 32 extend, and maintains the body in an upright position while sitting or standing.

Also illustrated in FIGS. 1 and 2, the spinal segment 4 includes intervertebral discs 20 that separate adjacent vertebra 5. The intervertebral discs 20 provide motion, load bearing and cushioning between adjacent vertebrae 5. Intervertebral discs 20 are the largest avascular structure in the body, relying on diffusion for nutrition. The diffusion of nutrients is aided by the compression cycles that the intervertebral discs 20 undergo during the course of normal movement, which drives out waste products and cycles fluids. Lying down and resting reduces the load on the intervertebral discs 20 allowing nutrients to diffuse into the intervertebral discs 20.

Also illustrated in FIGS. 1 and 2, the spinal segment includes spinal facet joints 16. Spinal facet joints 16 join the adjacent vertebrae 6. The spinal facet joints 16 are synovial joints that function much like those of the fingers. Together with the intervertebral disc 20, the spinal facet joints 16 function to provide proper motion and stability to a spinal segment 4. Thus, each spinal segment 4 includes three joints: the intervertebral disc 20 in the anterior aspect of the spinal segment 4 and the two spinal facet joints 16 in the posterior aspect of the spinal segment 4.

For the spinal segment 4 to be healthy, each of the intervertebral disc 20 and the spinal facet joints 16 must be healthy. To remain healthy these joints require motion. The intervertebral disc 20 and the spinal facet joints 16 function together to provide both quality and quantity of motion. The quality of the motion is exhibited by the non-linear energy storage (force-deflection, torque-rotation) behavior of the spinal segment 4. The quantity of motion is the range of segmental rotation and translation.

As an individual ages, natural changes occur in his musculoskeletal system. Specific to this discussion, the intervertebral discs and adjacent soft tissues of the spinal column become lax. For example, the spinal disc relies on a fluid filled nucleus to provide proper stability to the spinal segment and as fluid is lost from the nucleus the spinal segment becomes less stable. A decrease in spinal stability can become painful and can trigger a cascade of degenerative changes.

Back pain due to diseased, damaged, and/or degraded intervertebral discs 20 and/or spinal facet joints 16 is a significant health problem in the United States and globally. A non-exhaustive and non-limiting illustration of examples of diseased and/or damaged intervertebral discs is shown in FIG. 3. While a healthy intervertebral disc 20 is illustrated at the top of the spine segment 18, diseased and/or damaged discs are also illustrated. The diseased and/or damaged discs include a degenerated disc 22, a bulging disc 24, a herniated disc 25, a thinning disc 26, discs indicating symptoms of degeneration with osteophyte formation 28, as well as hypertrophic spinal facets 29.

A degenerating spinal segment 18 is believed to be the product of adverse changes to its biochemistry and biomechanics. These adverse changes create a degenerative cascade affecting the quality and/or quantity of motion and may ultimately lead to pain. For example, as the health of a spinal segment 18 degenerates and/or changes, the space through which the spinal cord 30 and peripheral nerves 32 (FIGS. 1 and 2) pass can become constricted and thereby impinge a nerve, causing pain. For example, the spinal cord 30 or peripheral nerves 32 may be contacted by a bulging disc 24 or herniated disc 25 or hypertrophic spinal facet 29 as illustrated in FIG. 3. As another example, a change in the spinal segment 18, such as by a thinning disc 26 may alter the way in which the disc functions, such that the disc and spinal facets may not provide the stability or motion required to reduce muscle, ligament, and tendon strain. In other words, the muscular system is required to compensate for the structural deficiency and/or instability of the diseased spinal segment 18, resulting in muscle fatigue, tissue strain, and hypertrophy of the spinal facets, further causing back pain. The pain this causes often leads patients to limit the pain-causing motion. However, this limiting of motion, while offering temporary relief, may result in longer-term harm because the lack of motion limits the ability of the disc to expel waste and obtain nutrients as discussed above.

In many instances of degenerative disc disease, fusion of the vertebrae is the standard of care for surgical treatment, illustrated in FIG. 4. In the U.S. alone in 2005, approximately 349,000 spinal fusions were performed at an estimated cost of $20.2 billion. The number of lower back, or lumbar, fusions performed in the U.S. is expected to grow to approximately 5 million annually by the year 2030 as the population ages, an increase of 2,200%.

Spinal fusion aims to limit the movement of the vertebra that are unstable or causing a patient pain and/or other symptoms. Spinal fusion typically involves the removal of a diseased disc 50, illustrated in outline in FIG. 4. The removed disc 50 is replaced by one or more fusion cages 52, which are filled or surrounded by autograft bone that typically is harvested by excising one or more spinal facet joints 57. Vertebral bodies 51 adjacent the removed disc 50 are stabilized with one or more posterior supports 58 that are fixedly connected to the vertebral bodies 51 with the use of pedicle screws 54 that are screwed—such as by use of a bolt-style head 56 to turn the pedicle screw 54—into a hole drilled into the pedicle 12 of the vertebral bodies 51.

Fusion, however, often fails to provide adequate or sufficient long-term relief in about one-half of the treatments, resulting in low patient satisfaction. Further, fusion, by definition, restricts the overall motion of the treated functional spine unit, imposing increased stresses and limiting range of motion on those portions of the spinal segment adjacent to the fused vertebral bodies 51. Fusion of a spinal segment has been indicated as a potential cause of degeneration to segments adjacent to the fusion. The adjacent spinal facet joints 57 and adjacent discs 59 often have to bear a greater load as a result of the fusion than would typically be the case, leading to possible overloading and, in turn, degeneration. Thus, surgical fusion often provides short-term relief, but possibly greater long-term spinal degradation than would otherwise have occurred.

Thus, a challenge to alleviating the back pain associated with various ailments is to find an intervertebral disc prosthesis that provides sufficient freedom of movement to at least reduce the risk to the functional health of the adjacent spinal segments, and/or facet joints, and/or discs that are otherwise compromised or have their functional health degraded by spinal fusion, and, more preferably, maintain the functional health of the adjacent spinal segments and/or facet joints and/or discs. Further, an intervertebral prosthesis optionally provides sufficient stability to the diseased segment to alleviate pain and/or other symptoms.

A further challenge is simply the complex, multi-dimensional nature of movement associated with a functional spine unit. Illustrated in FIG. 5 are the varying axes around which a functional spine unit moves. For example, a vertebra 5 is illustrated with an X-axis 60, around which a forward bending motion, or flexion, 61 in the anterior direction occurs. Flexion 61 is the motion that occurs when a person bends forward, for example. A rearward bending motion, or extension, 62 is also illustrated. The Y-axis 63 is the axis around which lateral extension, or bending, 64, left and right, occurs. The Z-axis 65 is the axis around which axial rotation 66, left and right, occurs. Spinal fusion, as discussed above, limits or prevents flexion 61-extension 62, but also limits or prevents motion in lateral extension, or bending, 64 and axial rotation 66. Thus, an improved alternative remedy to fusion preferably allows for movement with improved stability around each of the three axes, 60, 63, and 65.

Another difficulty associated with the complex motion of the spine is that the center-of-rotation for movement around each of the X-axis 60, Y-axis 63, and Z-axis 65 differs for each axis. This is illustrated in FIG. 6, in which the center-of-rotation for the flexion 61-extension 62 motion around the X-axis 60 is located at flexion-extension center-of-rotation 70. The center-of-rotation for the lateral extension, or bending, 64 motion around the Y-axis 63 is located at lateral extension, or bending, center-of-rotation 73. The center-of-rotation for the axial rotation 66 around the Z-axis 65 is located at axial rotation center-of-rotation 75. For more complex motion patterns (e.g., combined flexion, lateral extension/bending, etc.) a two-dimensional representation of the center-of-rotation is inadequate, but the three-dimensional equivalent called the helical axis of motion, or instantaneous screw axis can be employed. Intervertebral disc prostheses that force rotation of a spinal segment around any axis other than the natural helical axis impose additional stresses on the tissue structures at both the diseased spinal segments and the adjacent spinal segments. Compounding the issue for the centers-of-rotation is that they actually change location during the movement, i.e., the locations of the centers-of-rotation are instantaneous, which is sometimes referred to as the helical axis. Thus, a preferable remedy to spinal problems would account for the helical axis throughout the range of motion. Stated differently, a preferable intervertebral disc prosthesis would allow the diseased spinal segment and adjacent spinal segments to undergo motion approximate that of the natural helical axis through the range of motions.

Many previous efforts have been made to solve at least some of the problems associated with spinal fusion, but with varying degrees of success. For example, U.S. Pat. No. 8,308,801 issued on Nov. 13, 2012 discloses an intervertebral disc prosthesis that provides for motion in two directions, typically flexion-extension and lateral extension/bending, but not for axial rotation.

Thus, an emerging surgical option to spinal fusion is disc arthroplasty. The aim of disc arthroplasty is to restore stability to the painful segment without accelerating degeneration of the adjacent segments. The key in accomplishing this goal is to provide the proper amount of stability in each mode of loading to each specific patient need. If the surgically provided stability is wrong in any plane of motion then the pain and degeneration can continue.

BRIEF SUMMARY OF THE INVENTION

Each individual has a unique stiffness and range of motion in each of their joints. The stiffness and range of motion determine the joint's stability. Further, the stiffness and range of motion of each joint is unique in each mode of loading. An adjacent joint might respond differently to the same load. Surgically restoring each joint to its safe zone requires a surgical implant with patient and joint specific stability. Otherwise, the operative joint and the joints adjacent to it are likely to experience continued pain and degeneration.

Embodiments of the present total disc replacement system provide a surgical implant that is unique in its ability to restore proper stability in each joint's several planes of motion. Specifically, the such embodiments provide specific, tailored stiffness and range of motion in flexion/extension, lateral bending, axial rotation and in compression. Each plane of motion can be independently varied to controllable metrics.

Performing pre-operative range of motion studies on the spinal joints of an individual will provide the metrics needed to tailor the stiffness and range of motion of the present total disc replacement. For example, a flexion/extension study can be conducted by employing x-ray to reveal spinal range of motion limits. Then the flexion/extension controlling flexures of the present total disc replacement can be adjusted to those limits. The shape (both along the flexure and across) of the flexures and contact surface determines their stiffness and also their range of motion.

Embodiments of the present technology are unique in that the several planes of motion are decoupled within the device and can each be specifically tailored to match the patient's needs. That is to say that each flexure of the device can be individually shaped to provide proper motion as revealed by pre-operative diagnosis of the patient.

A pre-operative study of a patient might reveal that the non-symptomatic spinal segments experience a certain amount of flexion-extension, a certain amount of lateral bending, and a certain amount of axial rotation. The thickness, width, length and/or shape of the flexures of the present total disc replacement can then each be specifically shaped to provide the same metrics. Being that embodiments of the present total disc replacement provide an assembly of flexures, the device can be quickly built after a patient study and prior to surgery.

In accordance with one embodiment, the invention provides a method of tailoring a spinal implant to correspond to a specific patient's needs, including pre-operatively evaluating a patient to determine a desired spinal segment response and modifying one or more features of flexures of an implant to provide the desired spinal segment response.

Modifying one or more features of flexures of the implant can include modifying one or more of a thickness, width, length and/or shape of the features of the flexures.

The invention also provides various systems for executing the methods outlined herein.

Various features and embodiments of the invention disclosed herein provide robust and durable intervertebral disc prostheses that accommodate motion in three axes as compared to a single axis and/or double axes of motion of the prior art.

Embodiments of the invention include a spinal implant, such as an intervertebral disc prosthesis to replace an intervertebral disc that is removed from between two vertebra. Thus, embodiments of the spinal implant optionally are positioned between a first and a second vertebra. The spinal implant includes a first rolling-contact core that is operably coupled to the first vertebra. The rolling-contact core includes a convex surface having a first axis, the convex surface providing a rolling motion in a first direction to the vertebra coupled to the rolling-contact core relative to a second vertebra. At least one flexure optionally connected to the first rolling-contact core constrains, at least in part, the rolling motion of the first rolling-contact core. The flexure may be modified or formed during construction with respect to one or more of thickness, width, length, and/or shape to provide a desired stiffness and/or displacement to the spinal implant in one or more of flexion-extension or lateral bending.

Optionally, embodiments of the invention include a second rolling-contact core that is operably coupled to the first rolling-contact core. The second rolling-contact core also includes a second convex surface having a second axis rotated from the first axis, the second convex surface providing a rolling motion in a second direction to the first vertebra relative to the second vertebra. At least another flexure optionally connected to the second rolling-contact core constrains, at least in part, the rolling motion of the second rolling-contact core. The other flexure may also be modified or formed during construction with respect to one or more of thickness, width, length, and/or shape to provide a desired stiffness and/or displacement to the spinal implant in one or more of flexion-extension or lateral bending.

In various embodiments, at least one of the flexures and the rolling-contact cores are coupled or secured directly to the vertebra. Alternatively, embodiments of the invention include end plates, to which the flexures and rolling-contact cores are coupled. The end plates are secured to the first and second vertebra, thereby coupling the rolling-contact cores to the vertebrae.

Optionally, embodiments of the spinal implant include an axial-rotation core operably coupled to at least the first rolling-contact core. The axial-rotation core is configured to provide rotation to the first vertebra relative to the second vertebra around an axis orthogonal to the first axis and/or the second axis. The axial-rotation core optionally includes another flexure connected thereto that constrains, at least in part, the rotation. This other flexure may be modified or formed during construction with respect to one or more of thickness, width, length, and/or shape to provide a desired stiffness and/or displacement to the spinal implant in axial rotation.

In addition to considerations of tailoring the implant to patient-specific needs determined during the pre-operative study, the implant may also be tailored to take into consideration a desired surgical approach. For example, the stiffness of the spinal implant may be modified to account for lost stability caused by a desired surgical approach.

Embodiments of the spinal implant include a geometry that, once implanted, is configured to allow flexion-extension, and/or lateral extension/bending, and/or axial rotation with an instantaneous or near-instantaneous centers-of-rotation for the diseased and/or damaged spinal segment and/or adjacent vertebrae and/or spinal facet joints and/or discs that are similar to that of a healthy spinal segment. Thus, the spinal implant restores, to a degree, close to normal movement of the diseased and/or damaged spinal segment and adjacent vertebrae and/or spinal facet joints and/or discs, which, in turn, aids in maintaining the health of adjacent vertebra and/or spinal facet joints and/or discs.

Other embodiments of the spinal implant provide protection to the spine, discs, spinal cord, and peripheral nerves by reducing the risk of harmful, damaging, and/or painful movements while still providing a sufficient range of motion to reduce the risk to adjacent vertebrae and/or spinal facet joints and/or intervertebral discs becoming diseased and/or damaged from lack of sufficient movement. Embodiments of the spinal implant do so by reducing the stresses on a diseased and/or damaged spinal segment from which an intervertebral disc is removed without overloading the adjacent spinal segments, including the adjacent intervertebral discs, spinal facet joints, and vertebrae, that could initiate progressive degeneration or diseases in the adjacent spinal segments.

Additionally, embodiments of the spinal implant preferably provide proper motion—such as the centers-of-rotation, whether instantaneous or otherwise, limits of the ranges-of-motion, and the types of motion—that are maintained near those of a functional spine unit to maintain an effective range of motion for the muscles and the tendons around the spine and to reduce the amount of spinal cord strain.

Embodiments of the spinal implant are preferably made of biocompatible materials, including, but not limited to, biocompatible polymers and plastics, stainless steel, titanium, nitinol, shape-memory materials and/or alloys, and other similar materials.

Embodiments of methods of using the spinal implant are also disclosed.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

Figure 1:
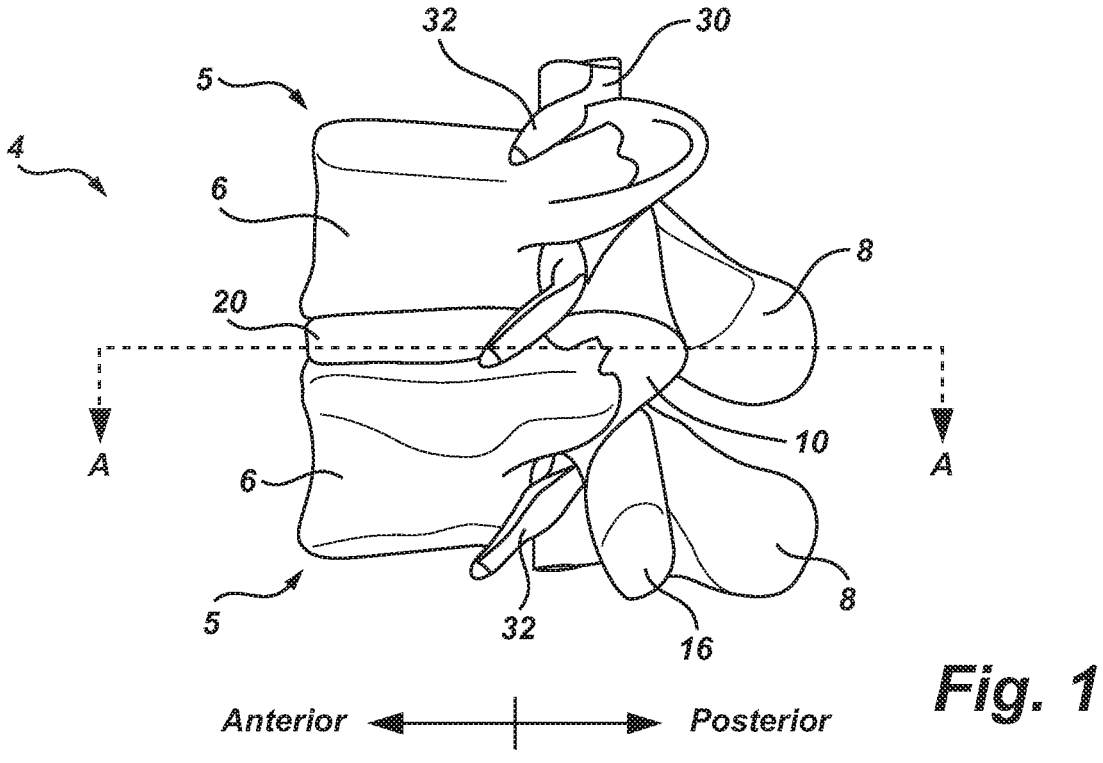
FIG. 1 is a segment of a functional spine unit.
Figure 2:
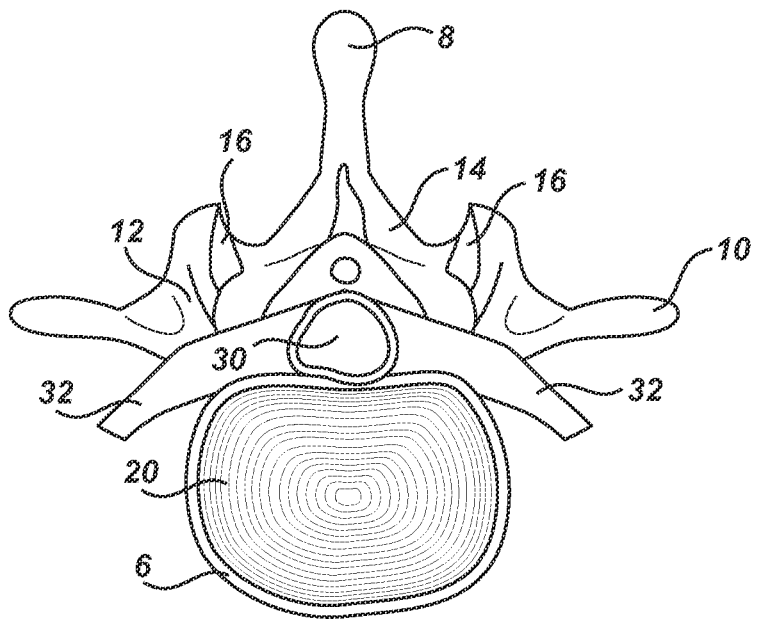
FIG. 2 is a cross-section of the segment of the functional spine unit illustrated in FIG. 1, taken along section A-A of FIG. 1.
Figure 3:
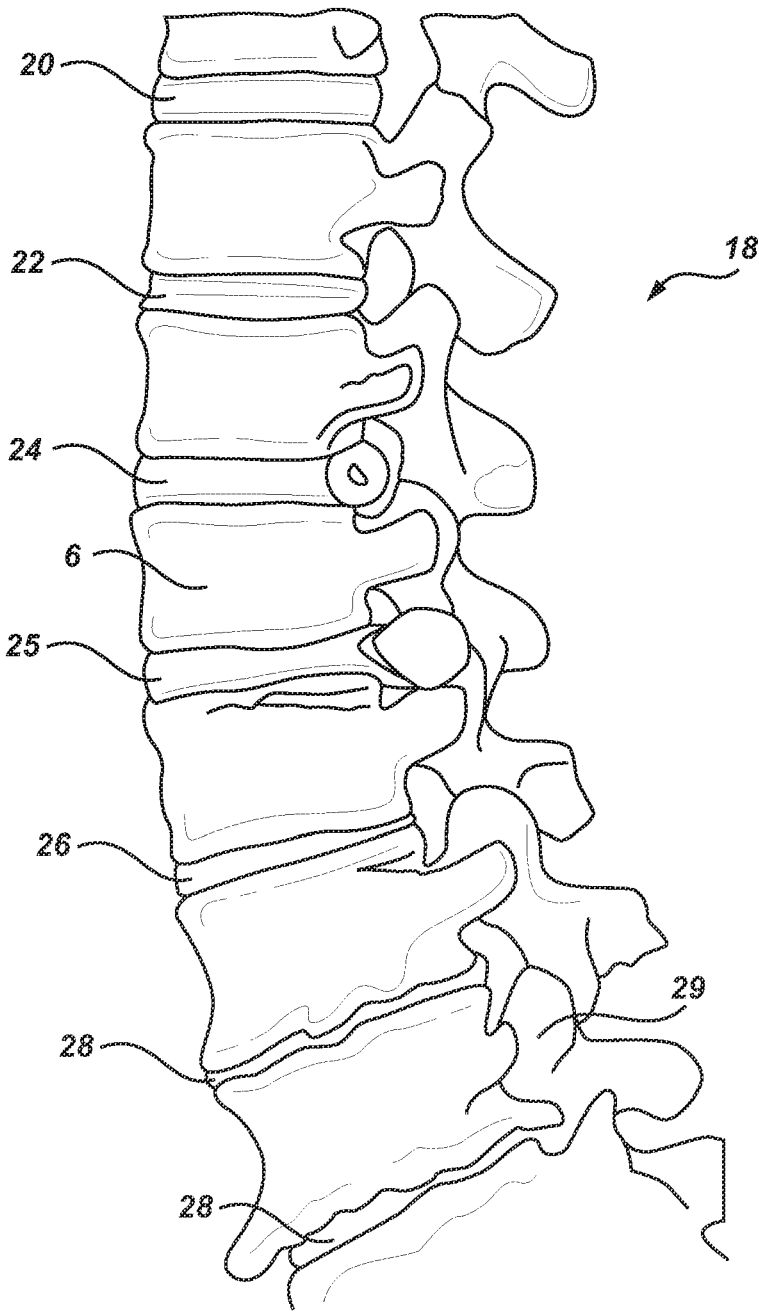
FIG. 3 is a segment of a spine illustrating various pathologies of intervertebral discs.
Figure 4:
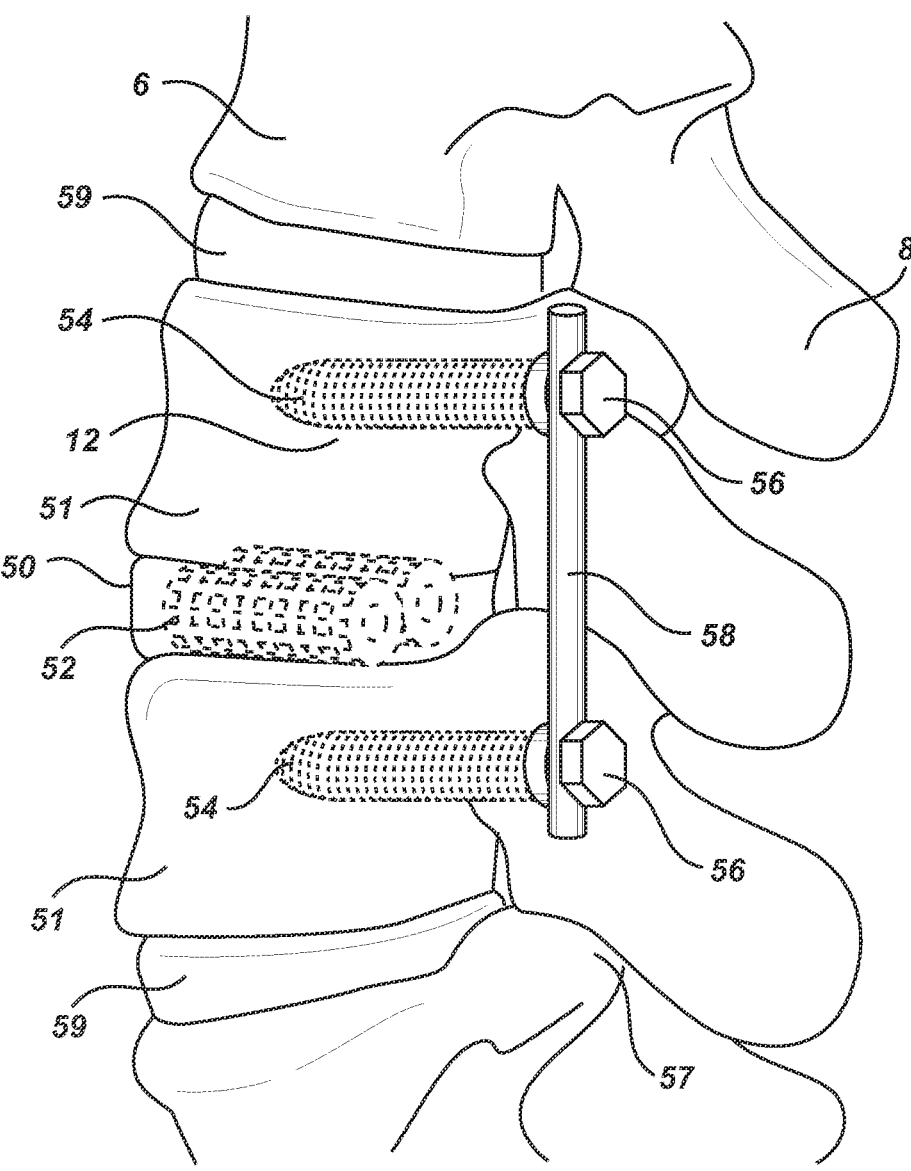
FIG. 4 is a prior art discectomy and spinal fusion.

The drawings are not necessarily to scale.

Reference will now be made to the exemplary embodiments illustrated, and specific language will be used herein to describe the same. It will nevertheless be understood that no limitation of the scope of the invention is thereby intended.

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

As used herein, the singular forms "a" and "the" can include plural referents unless the context clearly dictates otherwise. Thus, for example, reference to "a flexure" can include one or more of such flexures.

As used herein, the terms "attached," "coupled," "fixed," etc., can be used to describe a condition in which two or more components are coupled to one another in such a manner that they function as intended: that is, the force required to uncouple the components is sufficiently large such that the components will remain attached to one another during the service for which they were designed. In some embodiments of the invention, various components can be "permanently" coupled to one another: in such a case, the components are coupled to one another such that some deformation of one or both of the components, or the fasteners used to couple the components, will occur if the components are uncoupled from one another. One example of such a coupling can occur when two or more components are welded, bonded or otherwise adhered to one another.

In other aspects, various components can be "removably" coupled to one another such that they can be separated without causing permanent deformation of the components, or the fasteners used to couple the components. One example of such a coupling can occur when two or more components are threadably attached to one another (in which case, removal of threadable elements can result in uncoupling of the components without damaging the elements), or when a pin is used to secure one or more components in position relative to each other, or when two or more components are slidably insertable one within another to provide a telescoping relationship.

Directional terms, such as "proximal," "distal," "vertical," "horizontal," "upper," "lower," etc., are used herein to describe relative positions of various components, as those components are used in a patient. It is to be understood that such usage is an effort to most clearly describe, and, where applicable, claim, the features of the invention and is not be to limiting unless the context clearly indicates otherwise. Such directional terms are used in a manner that will be readily understood by one of ordinary skill in the art having possession of this disclosure.

As used herein, the term "substantially" refers to the complete or nearly complete extent or degree of an action, characteristic, property, state, structure, item, or result. As an arbitrary example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or subranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

As noted above, the kinetics and kinematics of the spine are quite complex, involving three separate axes around which motion occurs and three separate centers-of-rotation for the different motions. Many previous spinal implants often address just one form of motion, typically flexion and extension, often through the use of springs of some type that flex and compress. Efforts to address more than one mode of rotation or motion typically tend to be complex, large, and often do not address each individual motion as effectively as devices dedicated to a single motion. Even when efforts are made to address more than one mode of rotation, such efforts have not been patient-specific.

Figure 7:
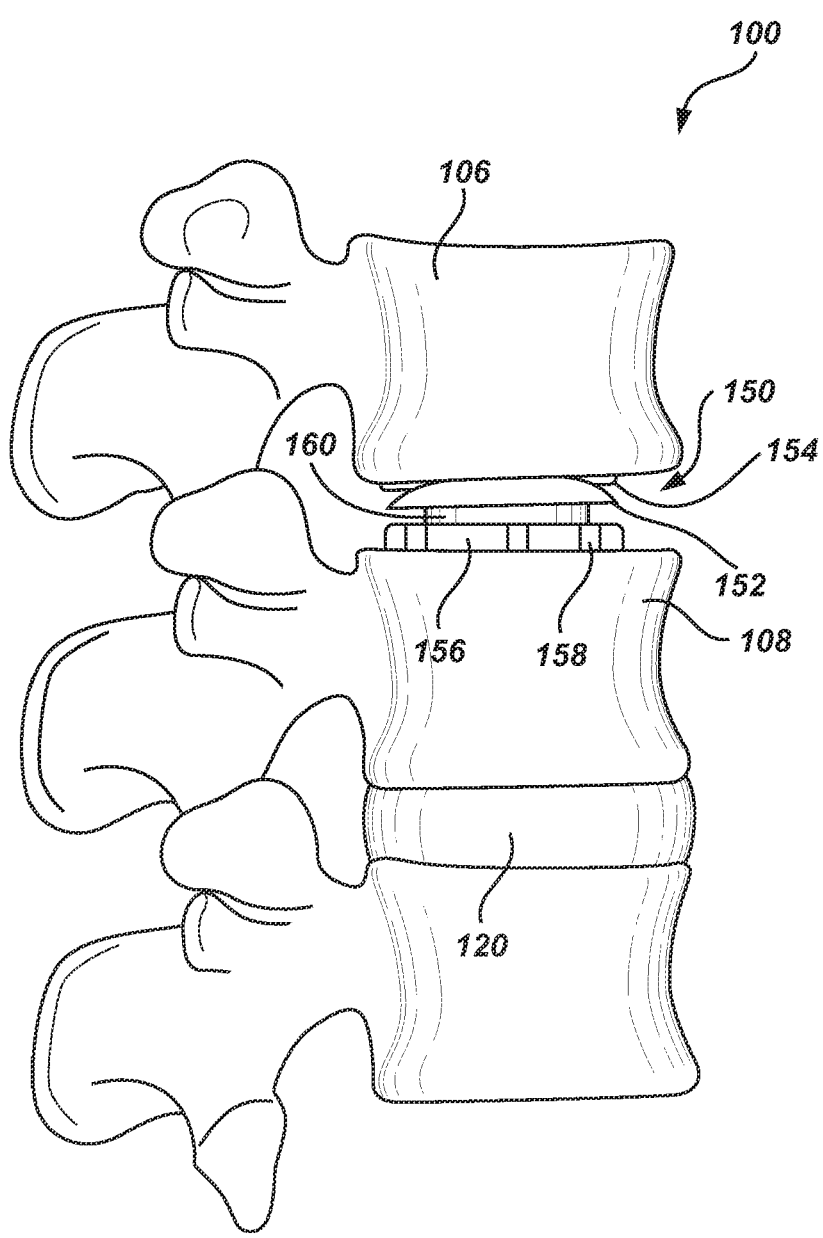
FIG. 7 illustrates an embodiment of a spinal implant, shown from the lateral/side view implanted and coupled directly to a first vertebra and a second vertebra.
Figure 8:
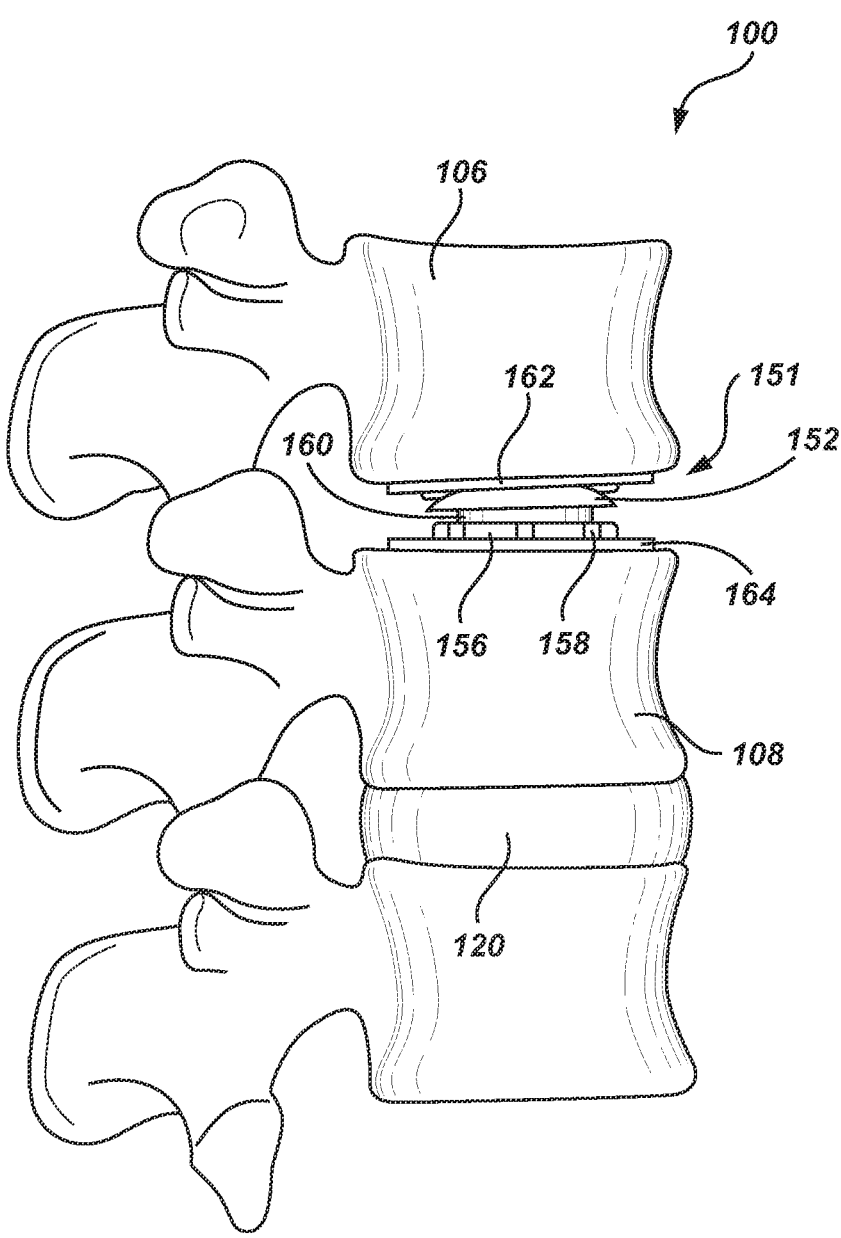
FIG. 8 illustrates an embodiment of a spinal implant, shown from the lateral/side view implanted and coupled to optional end plates, the end plates secured to a first vertebra and a second vertebra.

Turning to FIGS. 7 and 8, embodiments of a spinal implant 150 and 151, such as an intervertebral disc prosthesis, are illustrated positioned between a first vertebra 106 and a second vertebra 108 of a spinal segment 100 in a space where an intervertebral disc (e.g., intervertebral disc 120) has been removed.

Referring to FIGS. 7 and 8, each of the embodiments of the spinal implant 150, 151 include a first rolling-contact core 152. The first rolling-contact core 152 optionally includes at least one flexure 154. While FIGS. 7 and 8 illustrate one size and shape of flexure 154, it should be understood that the size, shape, stiffness, thickness, and contact surface may be modified pre-surgically to achieve a desired stiffness and/or range of motion, as discussed more fully below, so the specific size, shape, and/or number of flexure(s) 154 shown in FIGS. 7 and 8, or of any flexures shown in any of the Figures is intended only to be generally representational of one option for placement, size, and shape of such flexures. The spinal implant 150, 151 optionally includes a second rolling-contact core 156 that optionally includes at least another flexure 158. The spinal implant 151 in FIG. 8 optionally includes a first end plate 162 and a second end plate 164.

Figure 9:
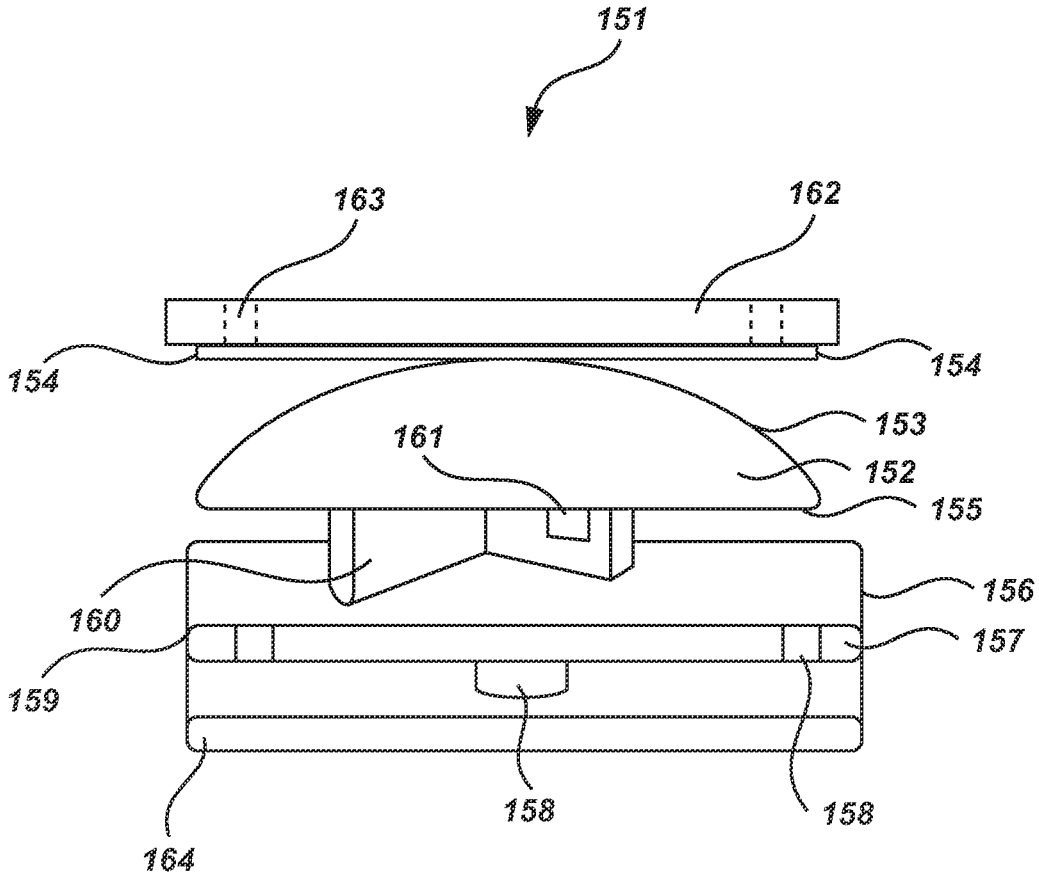
FIG. 9 illustrates lateral/side view of an embodiment of the spinal implant that optionally includes an axial-rotation core.
Figure 10:
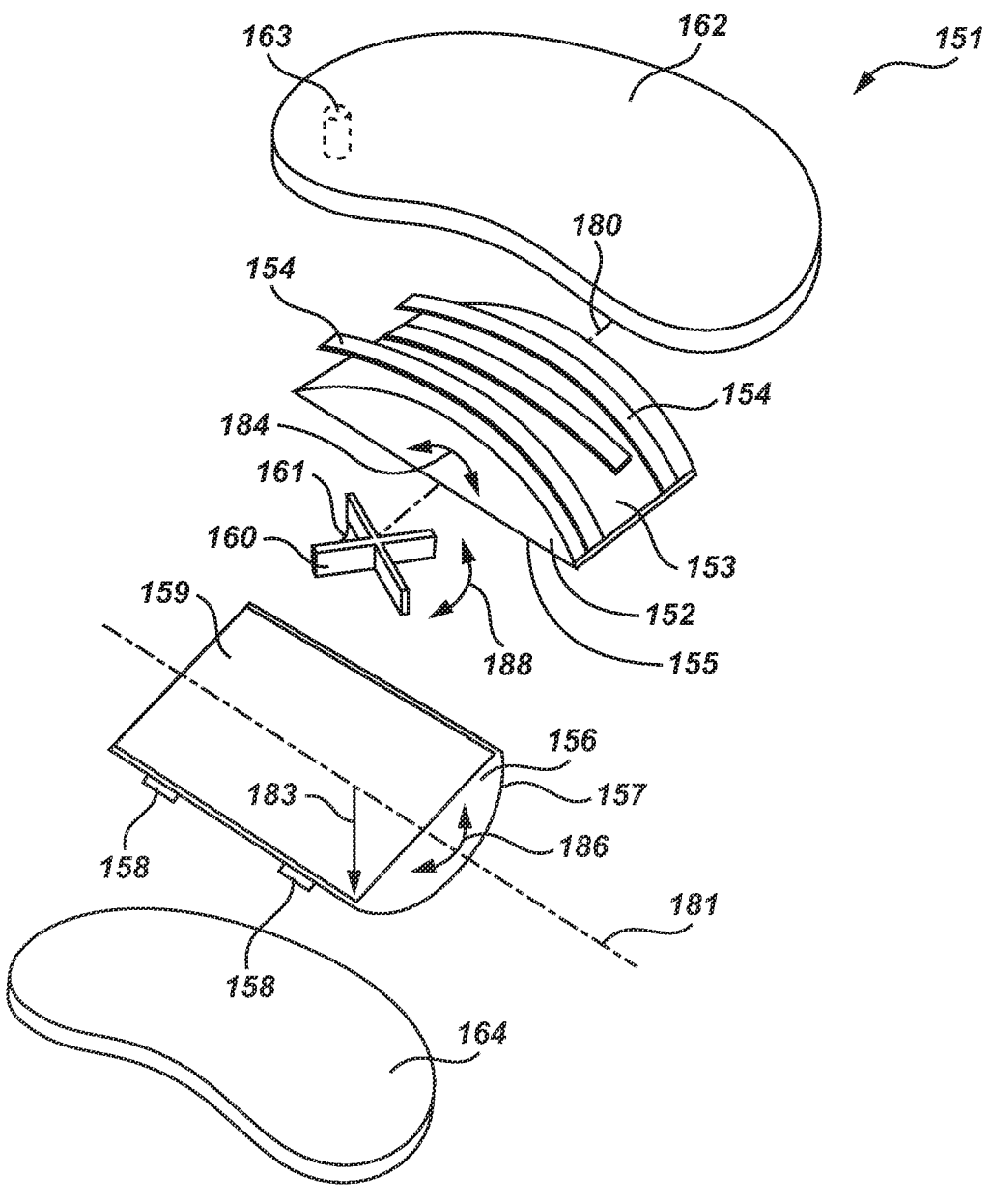
FIG. 10 is an exploded isometric view of the spinal implant of FIG. 9.
Figure 11:
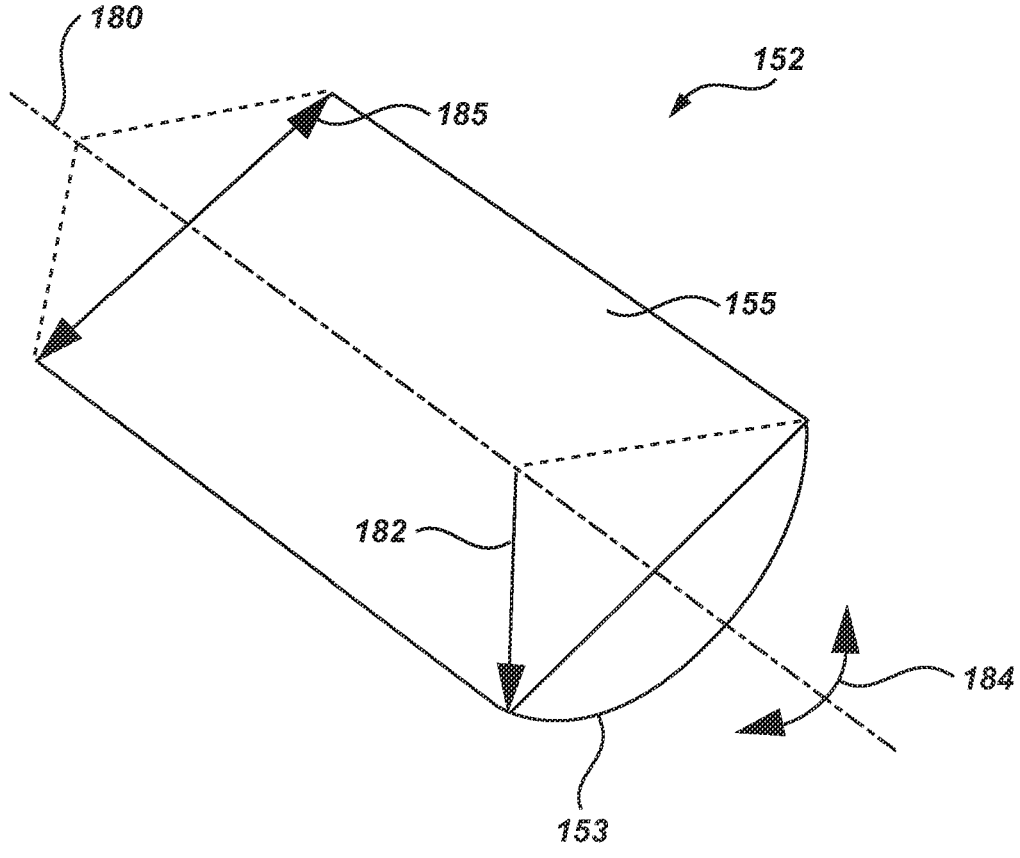
FIG. 11 is an isometric view of a rolling-contact core of the spinal implant of FIG. 9.

Further details of the embodiments of the spinal implant 150, 151 are illustrated in FIGS. 9-11. A first rolling-contact core 152 includes a first rolling surface 153 and a first chord surface 155, as best illustrated in FIG. 11. The embodiment of the first rolling surface 153 as illustrated is a portion of a cylindrical segment defined by a first radius of curvature 182 with a first axis 180, the first rolling surface 153 providing a first rolling motion in a direction 184. The first chord surface 155 is a plane through the cylindrical segment. The width 185 of the first rolling-contact core 152 can equal the diameter of the cylinder, or twice the first radius of curvature 182, in those embodiments in which the first chord surface 155 bisects the cylindrical segment through the first axis 180. While the first rolling surface 153 is illustrated to be defined by the first radius of curvature 182 and, therefore, circular in shape, it is understood that the first rolling surface 153 can be defined by a parabola, ellipsoid, toroid, hyperbolic, or other curved surface. The first rolling surface 153 can optionally be of a shape engineered and selected to provide a desired range of motion, instantaneous axis of rotation, helical axis of motion, kinematic response, resistance to motion, and the like.

Optionally, the spinal implant 150, 151 includes a second rolling-contact core 156, which includes a second rolling surface 157 and a second chord surface 159, as best illustrated in FIG. 10. The embodiment of the second rolling surface 157 as illustrated is a cylindrical segment defined by a second radius of curvature 183 with a second axis 181 that provides a second rolling motion in a direction 186. The second chord surface 159 is a plane through the cylindrical segment. While the second rolling surface 157 is illustrated to be defined by a second radius of curvature 183 and, therefore, circular in shape, it is understood that the second rolling surface 157 can be defined by a parabola, ellipsoid, toroid, hyperbolic, or other curved surface. The second rolling surface 157 can optionally be of a shape engineered and selected to provide a desired range of motion, instantaneous axis of rotation, helical axis of motion, kinematic response, resistance to motion, and the like. In addition, the second rolling surface 157 can be of a different geometry and have a different, second radius of curvature 183 (or other defining characteristic, such as the major and minor axis of an ellipsoid, or the focus of a parabola, as non-limiting examples) than the geometry and first radius of curvature 181 of the first rolling surface 155.

The second rolling-contact core 156, when included, is oriented such that the second axis 181 is rotated relative to the first axis 180 such that the second rolling motion occurs in a second, different direction 186 relative to the first rolling motion that occurs in the first direction 184. The first axis 180 and second axis 181 can be rotated relative to each other from about 0 degrees to about 180 degrees and, more preferably, from about 30 degrees to about 150 degrees and, more preferably still, from about 70 degrees to about 110 degrees, as well as orthogonal to each other. For example, a spinal implant 150, 151 can be provided that allows rolling motion in flexion-extension (e.g., around the X-axis 60 in FIG. 5), as well as lateral extension/bending (e.g., around the Y-axis 63 in FIG. 5).

The spinal implant 150, 151 can be formed of biocompatible plastics, polymers, metals, metal alloys, laminates, shape-memory materials, and other similar materials, either wholly as one material or as a combination of materials—i.e., different components may be manufactured from different materials and/or a single component, such as a rolling-contact core, can be manufactured of two or more materials, such as have a softer or resilient outer surface over a more rigid inner material. Optionally, the materials can be resilient. That is, the materials can have a varying and selectable degree of elastic deformation to provide cushioning between the vertebra 106 and 108 in order to mimic, at least in part, the cushioning that intervertebral discs 120 provide to the spinal segment 100.

Optionally, the first rolling-contact 152 core includes at least one flexure 154, and the second rolling-contact core 156 optionally includes at least another flexure 158. That is, one or more flexures 154, 158 can be used to create what may be referred to as a compliant mechanism or compliant spinal implant because its motion occurs, in part, through the flexible deflection of the flexures, as is described below. For example, FIGS. 9 and 10 illustrate the use of three flexures 154, 158 on the respective rolling-contact cores 152, 156. As illustrated, the flexures 154, 158 are disposed on the first rolling surface 153 and the second rolling surface 157, respectively, although they can be positioned elsewhere. The flexures 154, 158 optionally can be made from a different material or the same material as the rolling-contact cores. The flexures 154, 158 optionally can be formed as flexible bands of a resilient or elastic material. That is, the flexures 154, 158 optionally exhibit elastic, spring-like behavior. The flexures 154, 158 optionally can be formed of biocompatible plastics, polymers, metals, metal alloys, laminates, shape-memory materials, and other similar materials, either wholly as one material or as a combination of materials—i.e., different components may be manufactured from different materials.

The flexures 154, 158 optionally are formed by separating a strip of material from the respective rolling-contact core 152, 156. Alternatively, the flexures 154, 158 are coupled to the respective rolling surface 153, 157 by welding, adhesives, mechanical connectors, and the like at a first end of the flexure 154, 158. At another end of the flexure spaced apart from the first end, the flexure 154, 158 is coupled to either an end plate or directly to a vertebra through the use of bio-compatible adhesives, mechanical connectors, such as screws, welding, and the like.

The flexures 154, 158 provide, in part, a spring-like constraint to the rolling motion in the directions 184 and 186, respectively. That is, the further the rolling motion occurs, the greater the restoring force that the flexures 154, 158 impart to the rolling-contact core 152, 156 to return the rolling-contact core 152, 156 to a neutral or undeflected position. In addition, the flexures 154, 158, maintain, in part, the relative position of the rolling-contact core 152, 156 to either the vertebrae 106, 108 and/or the end plates 162, 164. That is, the flexures 154, 158 allow rolling motion, but limit, in part, the ability of the rolling-contact core 152, 156 to move laterally, posteriorly, or anteriorly out of position relative to the vertebrae 106, 108.

The flexures 154, 158 as noted optionally couple the rolling-contact cores 152, 156 directly to the vertebrae 106, 108, whether through adhesives or mechanical devices, such as screws. The flexures 154, 158 can be attached at the vertebral end plate, within the area of the vertebra bounded by the vertebral end plate, or elsewhere on the vertebra, including the pedicles and/or the spinous process, and the like. The rolling surfaces 153, 157 would then roll directly upon the vertebra 106, 108.

Alternatively, the flexures 154, 158 can be coupled to the device end plates 162, 164 by mechanical devices, such as screws and the like, adhesives, welding, slots into which the ends of the flexures are retained, such as by clamping, and such other methods and systems. The rolling surfaces 153, 157 then roll upon a surface of the end plates 162, 164. The end plates 162, 164 can be square, rectangular, shaped like the vertebra 106, 108, as illustrated in FIG. 10, or other such shapes.

The end plates 162, 164 can be formed of biocompatible plastics, polymers, metals, metal alloys, laminates, shape-memory materials, and other similar materials, either wholly as one material or as a combination of materials, such as having a softer or resilient outer surface over a more rigid inner material. Optionally, the materials can be flexible and/or resilient. That is, the materials can have a varying and selectable degree of elastic deformation to provide cushioning between the vertebra 106 and 108 in order to mimic, at least in part, the cushioning that intervertebral discs 120 provide to the spinal segment 100. Further, resilient end plates 162, 164 optionally distribute the compressive load borne by the spinal implant 150 across a larger percentage of the area within the vertebral end plates, which may reduce the degree or the risk of remodeling of the cancellous tissue of the vertebra. Alternatively, the end plates 162, 164 optionally distribute the compressive load to the vertebral end plates.

The end plates 162, 164 operably couple the flexures 154, 158 and the rolling-contact cores 152, 156, respectively, to the first vertebra 106 and the second vertebra 108. More preferably, the end plates 162, 164 are not just operably coupled the vertebra, but also secured to the vertebra which indicates a direct connection to the vertebra, whereas operably coupled can include either a direct or indirect connection to the vertebra. The end plates 162, 164 can be secured via adhesives and/or mechanical devices, such as bone screws that can be installed in the optional through-holes 163 (FIG. 10). Optionally, threaded anchors can be screwed into the vertebra (and/or spinous process, and/or pedicles, and other such locations of the vertebra and spine), the threaded anchor then being threaded into a blind hole (not illustrated). Other similar examples of mechanical systems fall within the scope of the disclosure.

Figure 14:
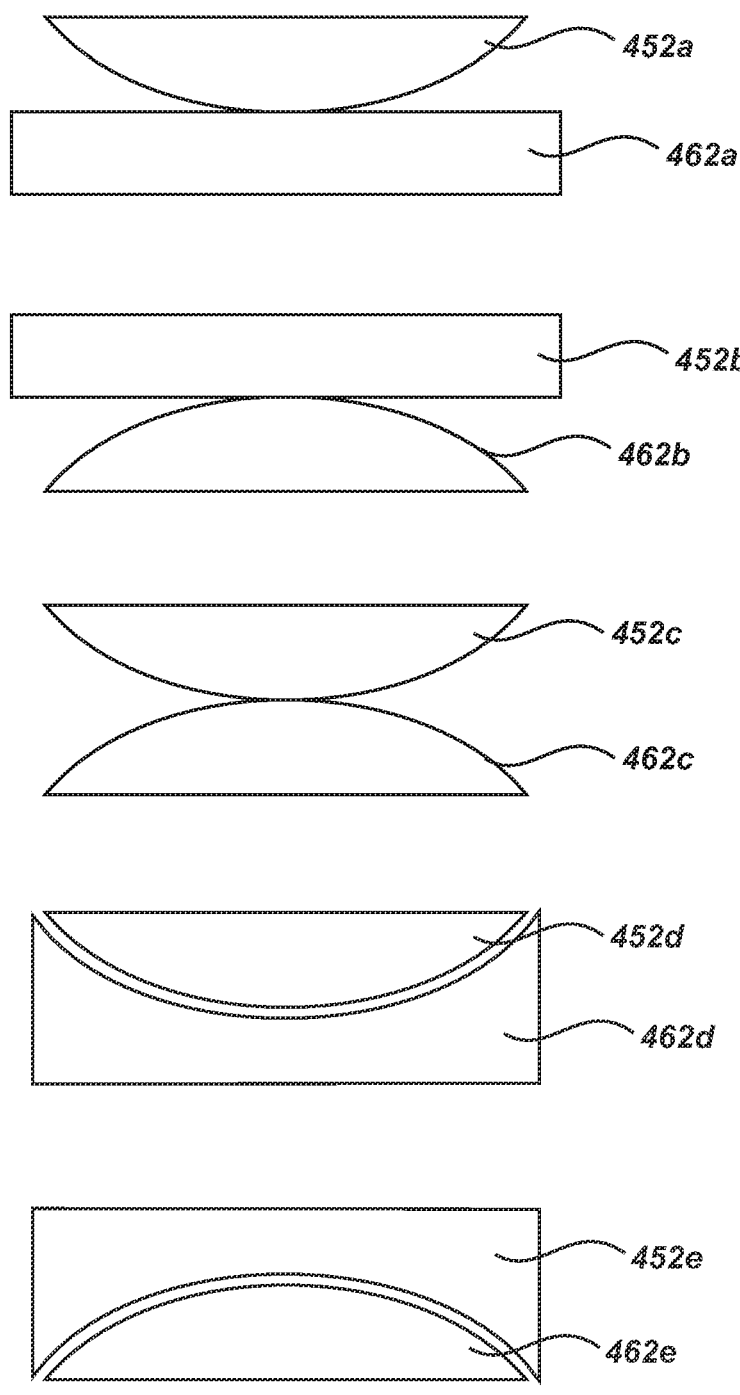
FIG. 14 is a side view of several embodiments of rolling-contact cores and end plates.

It is noted that the above embodiments describe rolling-contact cores 152, 156 that include a curved surface and end plates 162, 164 of substantially planar surfaces. Of course, other embodiments of rolling-contact cores and end plates fall within the scope of the disclosure. Non-limiting examples of such embodiments are illustrated in FIG. 14 and include: a rolling-contact core 452a that includes a convex surface and a substantially planar end plate 462a; a substantially planar rolling-contact core 452b and a convex end plate 462b; a convex rolling-contact core 452c and a convex end plate 462c; a convex rolling-contact core 452d and a concave end plate 462d; and a concave rolling-contact core 452e and a convex end plate 462e. Of course combinations, such as rolling-contact cores and end plates of different configurations and combinations fall within the scope of the disclosure. Further, these other embodiments of rolling-contact cores and end plates optionally use the flexures described above to constrain, at least in part, the motion of the rolling-contact cores. In addition, these other embodiments of rolling-contact cores and end plates optionally use an axial rotation core as described below.

Figure 5:
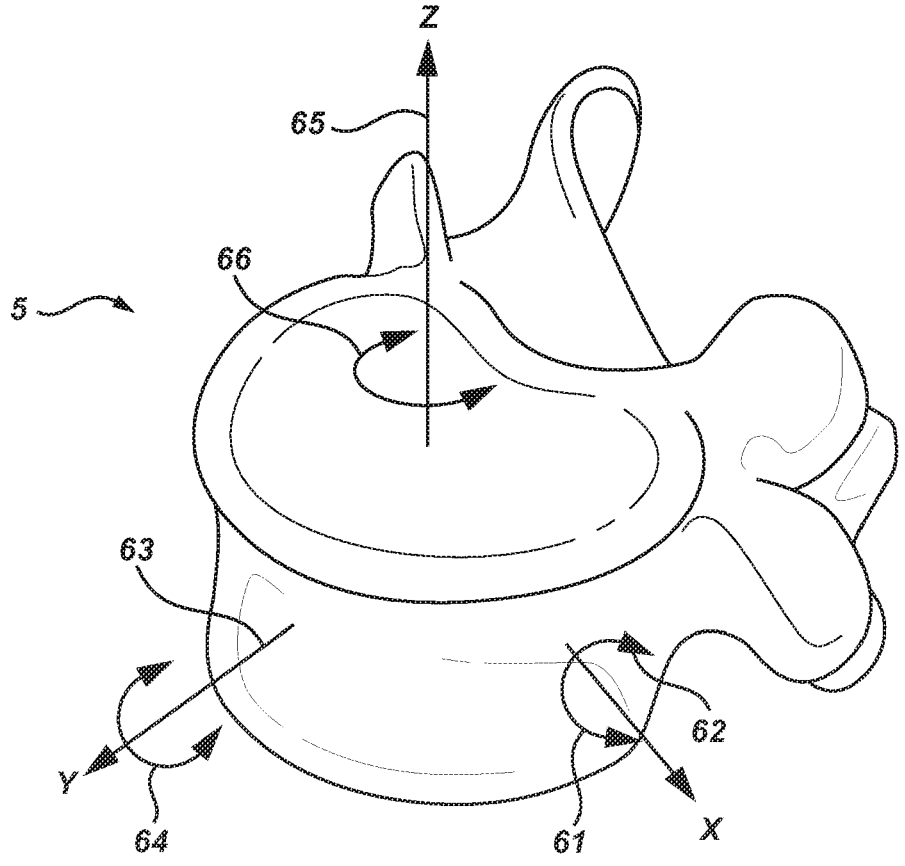
FIG. 5 illustrates the three axes of motion around which a functional spine unit moves.
Figure 6:
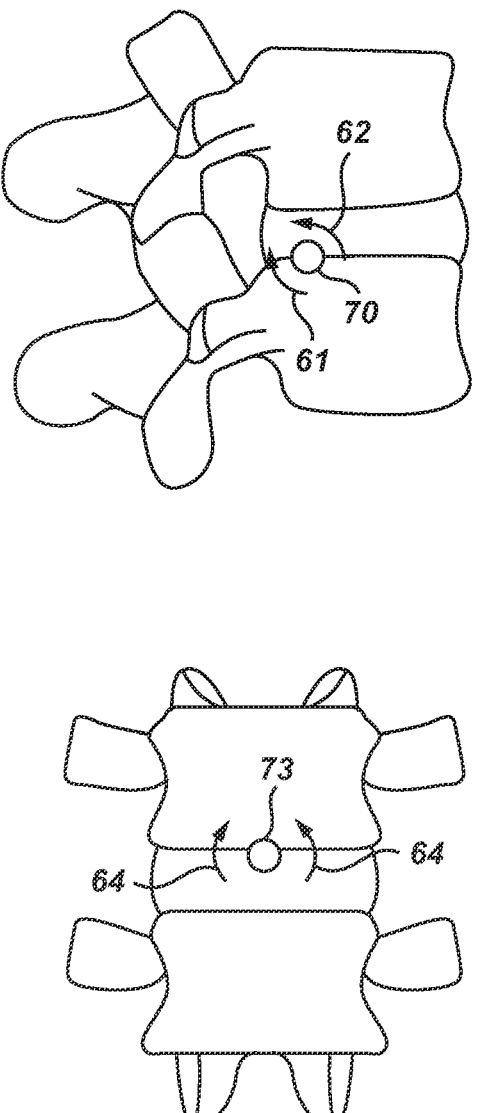
FIG. 6 illustrates the centers-of-motion of a functional spine unit.
Figure 6:
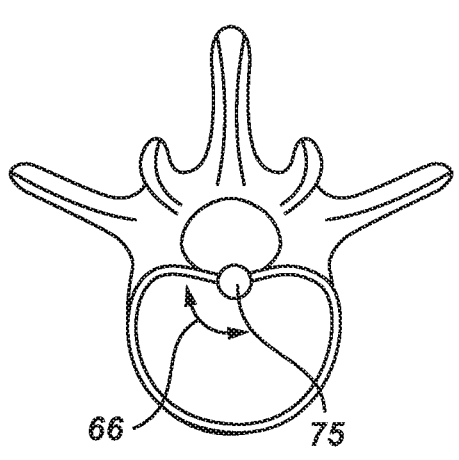
Figure 12:
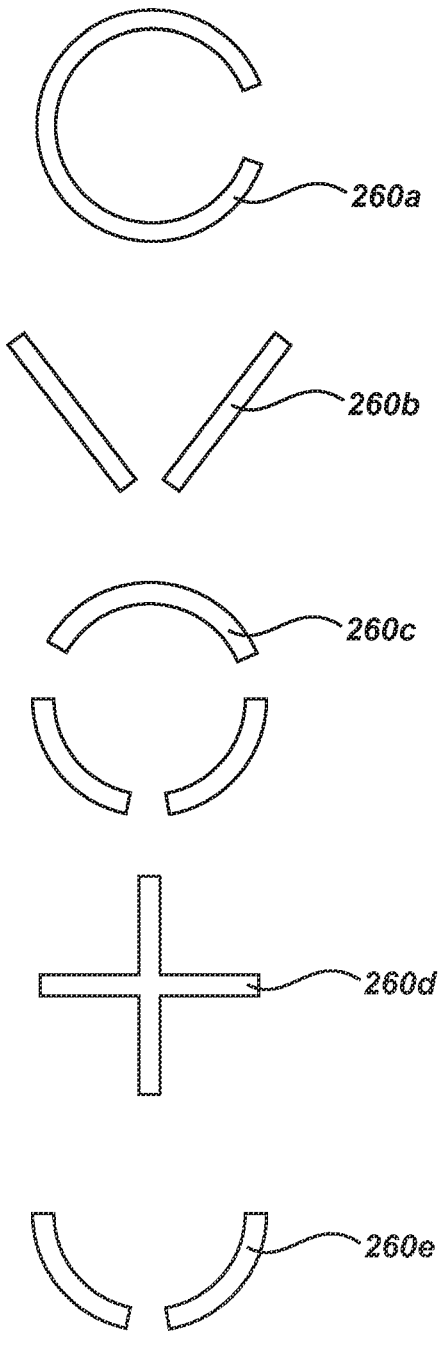
FIG. 12 is a top view of several embodiments of the axial-rotation core.

Optionally, the spinal implant 150, 151 includes an axial-rotation core 160 configured to provide axial rotation in a direction 188 (FIG. 10) of a first vertebra relative to a second vertebra, such as vertebra 106, 108, respectively. The axial rotation can, for example, occur around the Z-axis 65 as illustrated in FIG. 5, i.e., orthogonal to the first axis 180 and the second axis 181. The axial-rotation core 160 can optionally be of a shape engineered and selected to provide a desired range of motion, instantaneous axis of rotation, helical axis of motion, kinematic response, resistance to motion, and the like. For example, while FIGS. 9 and 10 illustrate an embodiment of an axial-rotation core 160 that is a cross or cruciform in shape, other non-limiting examples of embodiments include those illustrated in FIG. 12, such as 260a (a split-ring); 260b (a split-V); 260c (another split ring, in three portions); 260*d* (cross or cruciform); and 260*e* (one-half of split-ring). Other shapes fall within the scope of the disclosure.

The axial-rotation core 160 can be formed of biocompatible plastics, polymers, metals, metal alloys, laminates, shape-memory materials, and other similar materials, either wholly as one material or as a combination of materials. Optionally, the materials can be resilient. That is, the materials can have a varying and selectable degree of elastic deformation to provide cushioning between the vertebra 106 and 108 in order to mimic, at least in part, the cushioning that intervertebral discs 120 provide to the spinal segment 100. The axial-rotation core 160 can be formed to be an integral part of one or more of the rolling-contact cores 152, 156, or it can be a separate component coupled, either directly or indirectly, to the rolling-contact cores 152, 156, such as through the use of adhesives and mechanical connecting devices, such as screws, welding, and the like.

Embodiments of the axial-rotation core 160 include those that are positioned between a rolling-contact core and a vertebra (not illustrated) and/or an end plate 162, 164. Other embodiments include positioning the axial-rotation core 160 between two rolling-contact cores 152, 156 as illustrated in FIGS. 9 and 10. Other positions of the axial-rotation core 160 relative to the vertebra and the spinal implant 150, 151 and its components fall within the scope of the disclosure.

Optionally, the axial-rotation core 160 includes at least one axial or third flexure 161 and, optionally, more flexures 161. The axial flexure(s) 161 can be coupled, directly or indirectly, to various parts of the axial-rotation core 160, as illustrated in FIG. 10. Alternatively, the axial flexure 161 optionally can couple, in part, the axial-rotation core 160 to at least one of the rolling-contact cores, such as the first rolling-contact core 152 as illustrated in FIG. 9. In yet other embodiments, the axial flexure(s) 161 couple the axial-rotation core 160 to one or more of the end plates 162, 164 and/or the vertebra itself, such as the vertebra 106, 108, and/or its vertebral endplates, and/or the pedicles, and/or the spinous process, and the like. The coupling of the axial flexure(s) 161 optionally can be achieved through the use of mechanical devices, such as screws and the like, adhesives, welding, slots into which the flexures are retained, such as by clamping, and such other methods and systems.

The axial flexure(s) 161 optionally can be made from a different material or the same material as the axial-rotation cores 160. The axial flexure(s) 161 optionally can be formed as flexible bands of a resilient or elastic material. That is, the axial flexure(s) 161 optionally exhibit elastic, spring-like behavior. The axial flexure(s) 161 optionally can be formed of biocompatible plastics, polymers, metals, metal alloys, laminates, shape-memory materials, and other similar materials, either wholly as one material or as a combination of materials—i.e., different components may be manufactured from different materials.

The axial flexure(s) 161 provide, in part, a spring-like constraint to axial rotation in the direction 188. That is, the greater the axial rotation, the greater the restoring force that the axial flexure(s) 161 impart to the axial-rotation core 160 to return the axial-rotation core 160 to a neutral or undeflected position. In addition, the axial flexure(s) 161 maintain, in part, the relative position of the axial-rotation core 160 to either the vertebrae 106, 108 and/or the end plates 162, 164. That is, the axial flexure(s) 161 allow axial rotation, but limit, in part, the ability of the axial-rotation core 160 to move laterally, posteriorly, or anteriorly out of position relative to the vertebrae 106, 108.

Figure 13:
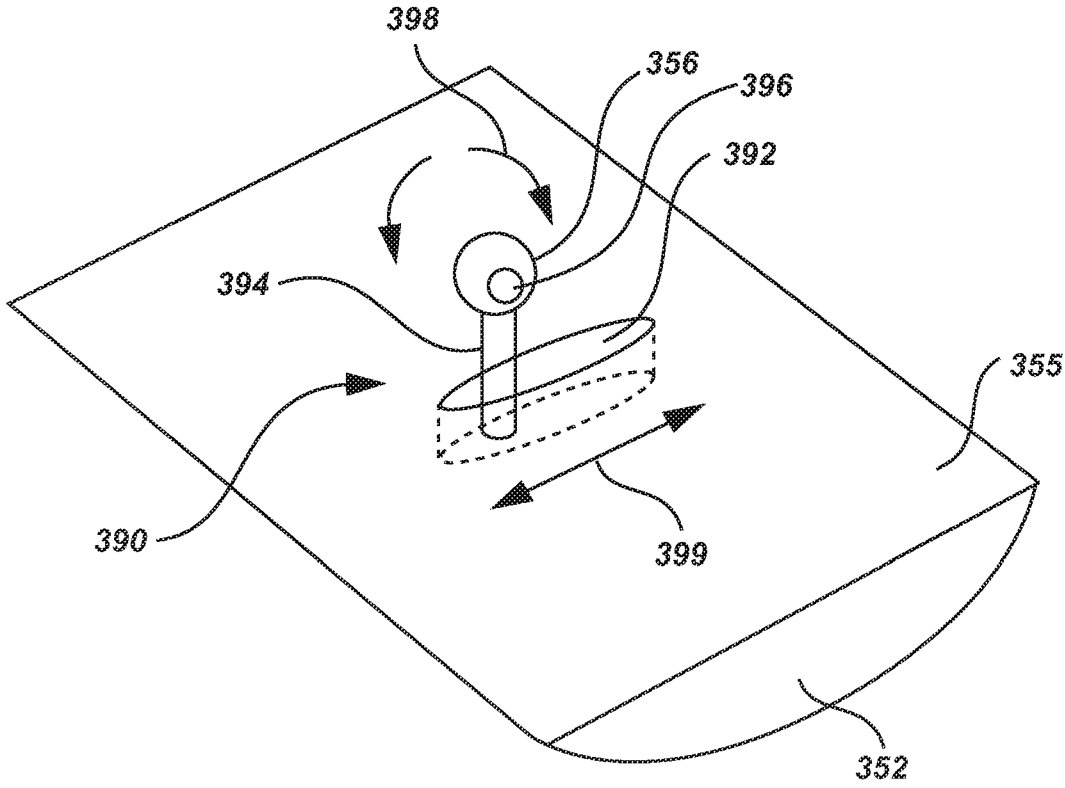
FIG. 13 is an isometric view of another embodiment, a pin-in-slot joint, of the axial-rotation core and an embodiment of a rolling-contact core.

Another embodiment of the axial-rotation core is illustrated in FIG. 13. The axial-rotation core 390 is a pin-in-slot joint. That is, the axial-rotation core 390 includes a slot 392 formed within the chord surface 355 of a rolling-contact core 352. The slot 392 is oriented to provide lateral movement in a direction 399 that, for example, may correspond to the Y-axis 63 in FIG. 5. A pin 394 is configured to be received and retained at a first end within the slot 392. The pin 392 is coupled at the connection 396 to, for example, a rolling-contact core 356, of which only a small portion is illustrated for clarity. The pin 394 is configured to rotate in a direction 398 around, for example, the Z-axis 65 in FIG. 5, thereby imparting a relative axial rotation between the rolling-contact cores 352, 356 and, consequently, the vertebrae coupled thereto. Thus, the axial-rotation core 390 provides a center-of-rotation that is capable of translation in a lateral direction while also providing axial rotation.

Optionally, the axial-rotation core 390 includes axial flexures (not illustrated in FIG. 13), such as those axial flexure(s) 161 discussed above.

Each individual has a unique stiffness and range of motion in each of their joints. The stiffness and range of motion determine the joint's stability. Further, the stiffness and range of motion of each joint is unique in each mode of loading, e.g. a joint might experience 12 degrees of flexion with a 2 Nm load and 6 degrees of lateral bending with a similar load. An adjacent joint might respond differently to the same load. Surgically restoring each joint to its safe zone requires a surgical implant with patient and joint specific stability. Otherwise, the operative joint and the joints adjacent to it are likely to experience continued pain and degeneration.

Embodiments of the present total disc replacement system provide a surgical implant that is unique in its ability to restore proper stability in each joint's several planes of motion. Specifically, embodiments of the present technology provide specific, tailored stiffness and range of motion in flexion/extension, lateral bending, axial rotation and in compression. Each plane of motion can be independently varied to controllable metrics.

Performing pre-operative range of motion studies on the spinal joints of an individual will provide the metrics needed to tailor the stiffness and range of motion of the present total disc replacement. For example, a flexion/extension study can be conducted by employing x-ray to reveal spinal range of motion limits. Then the flexion/extension controlling flexures of the present total disc replacement can be adjusted to those limits. The shape (both along the flexure and across) of the flexures and contact surface determines their stiffness and also their range of motion.

The present technology is unique in that the several planes of motion are decoupled within the device and can each be specifically tailored to match the patient's needs. That is to say that each flexure of the device can be individually shaped to provide proper motion as revealed by pre-operative diagnosis of the patient.

A pre-operative study of a patient might reveal that the non-symptomatic spinal segments experience, for example, 12 degrees of flexion-extension, 4 degrees of lateral bending, and 3 degrees of axial rotation. The thickness, width, length and/or shape of the various flexures of the present total disc replacement can then each be specifically shaped to provide the same metrics. Being that embodiments of the present total disc replacement include an assembly of flexures, the device can be quickly built after a patient study and prior to surgery.

Figure 15:
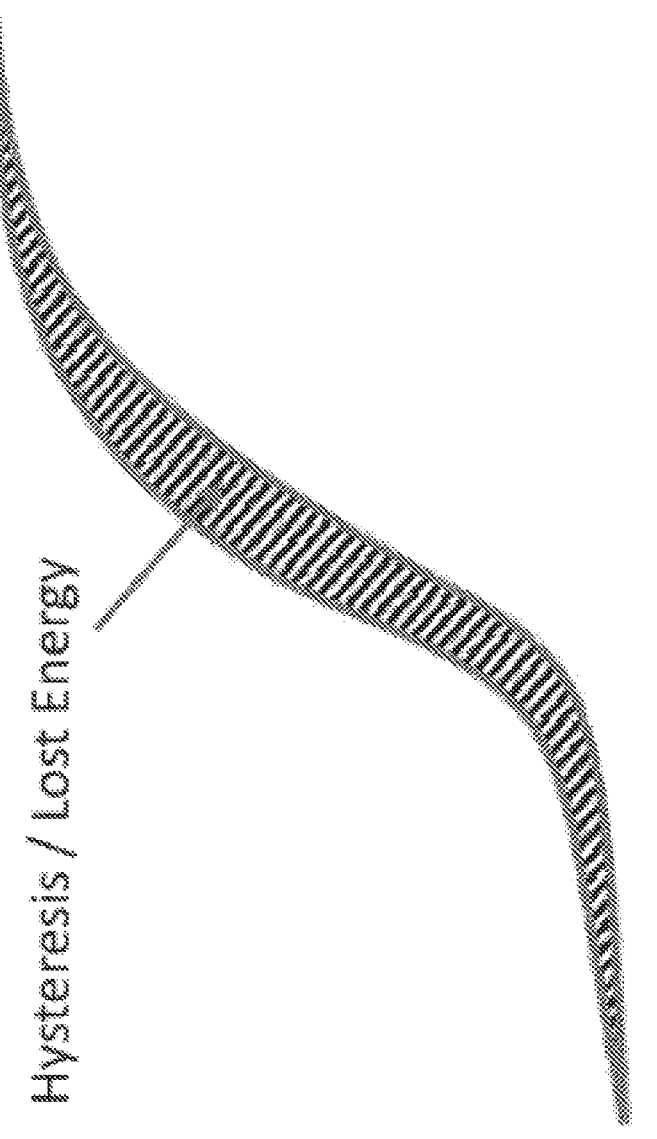
FIGS. 15-24 illustrate a method for determining metrics by which to tailor a spinal implant.
Figure 16:
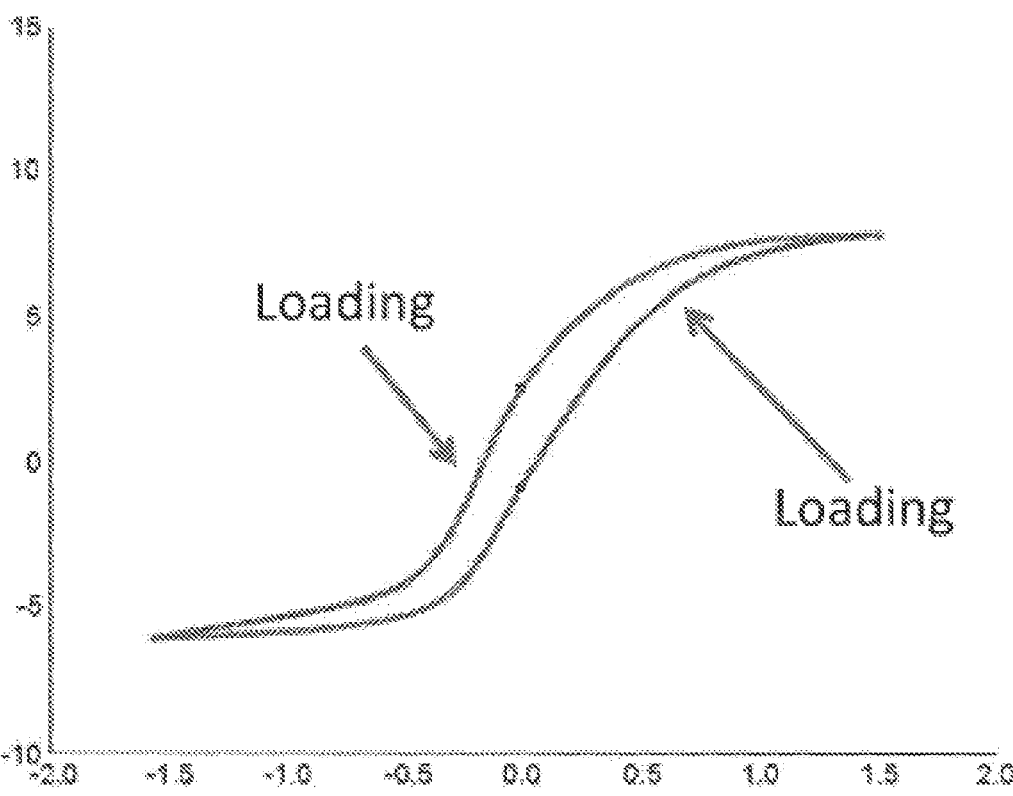
Figure 17:
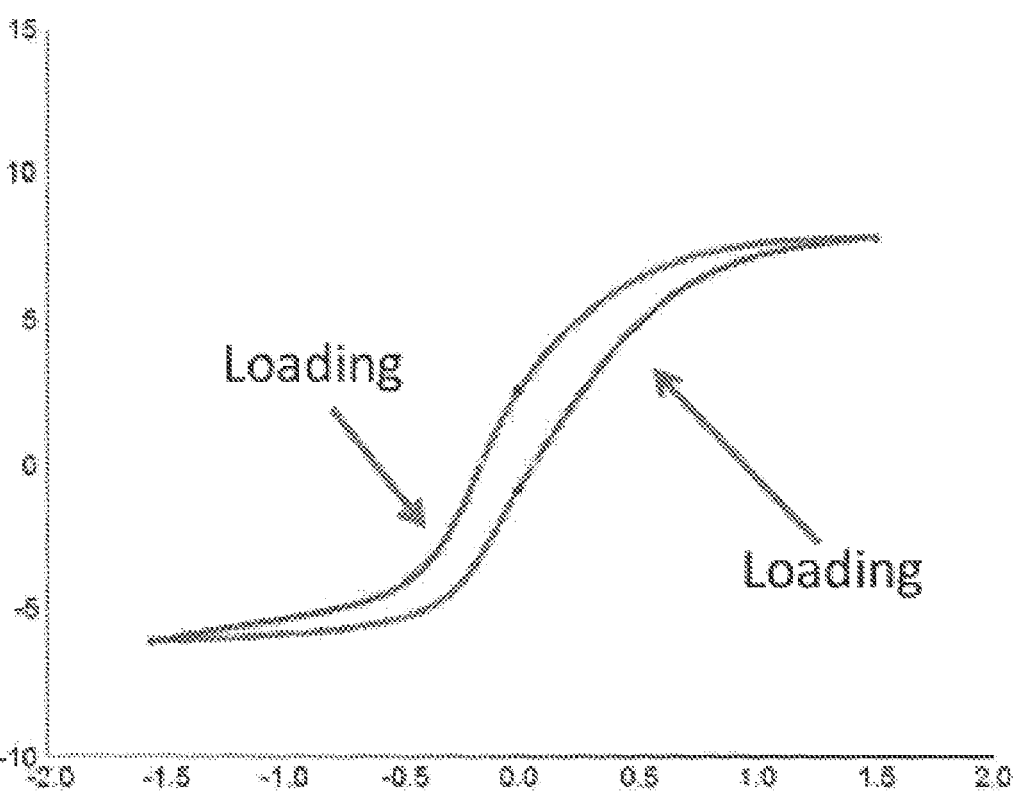
Figure 18:
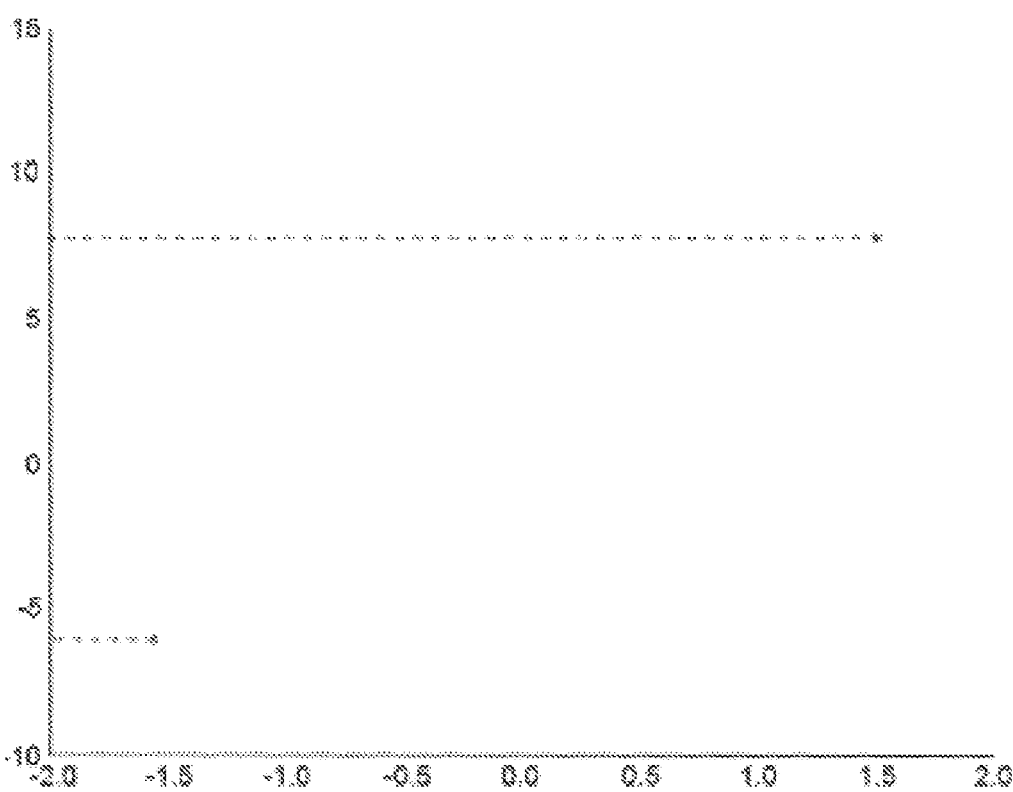

FIGS. 15-24 illustrate methods for determining how to tailor a spinal implant to achieve patient-specific stiffness and/or range of motion. FIG. 15 illustrates spinal kinetics of motion in a representative vertebral joint, which may be illustrated as a hysteresis curve as shown in the Figure. The space encompassed in the curve illustrates energy lost during the full range of motion. FIG. 16 illustrates force loading paths of the illustrative hysteresis curve, which may be difficult to obtain through traditional imaging. FIG. 17 illustrates displacement loading paths of the illustrative hysteresis curve, which may be easier to obtain through imaging.

According to embodiments of the invention, imaging of the region of the spine of interest may be obtained as the spine is manipulated within its range of motion (ROM) to determine various aspects of the range of motion under various loads. In a first step illustrated in FIG. 18, the full range of motion may be established by reviewing x-ray imaging under final load in each direction. The final load may be varied depending on the region of the spine of interest, the individual, or any other desired reasons, as will be appreciated by those of ordinary skill in the art. For example, a final load may be approximately 1.5 Nm in the cervical spine region, and 10 Nm in the lumbar spine region.

Figure 19:
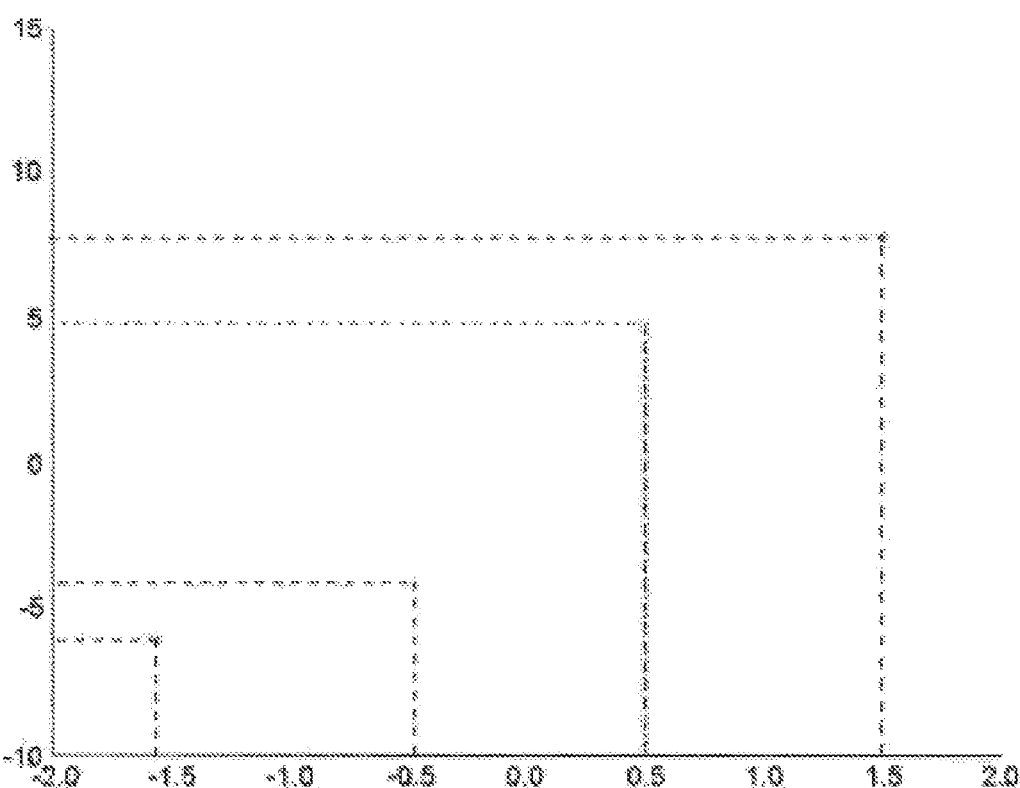

Next, the high flexibility zone loading knees may be established by reviewing x-ray imaging of the spinal segment of interest using either or both of a percentage of the full range of motion (e.g., approximately two thirds of the full range of motion) or as a low-load range of motion (e.g., under 0.5 Nm load). This step is illustrated in FIG. 19.

Figure 20:
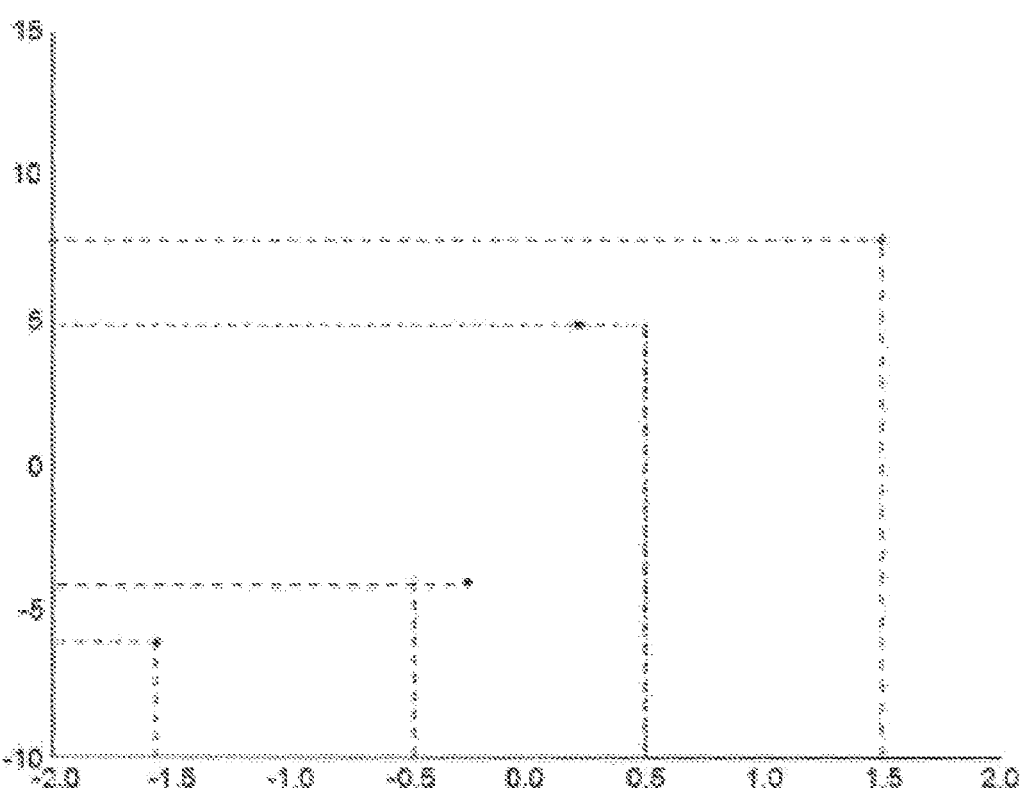
Figure 21:
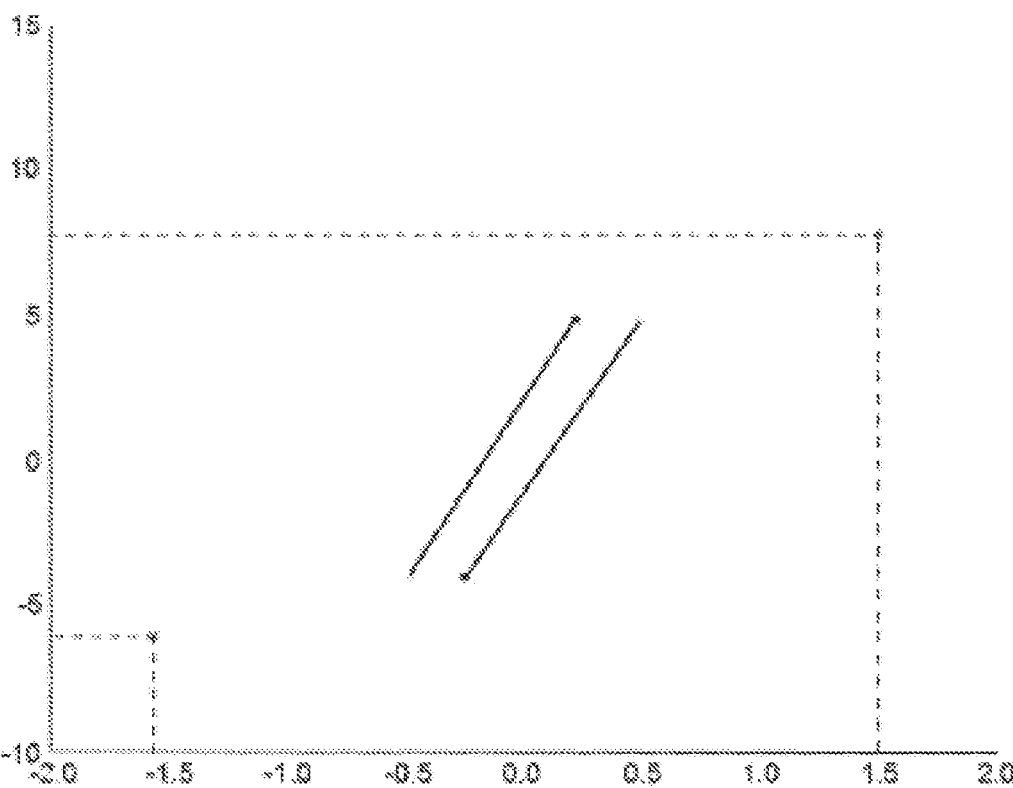
Figure 22:
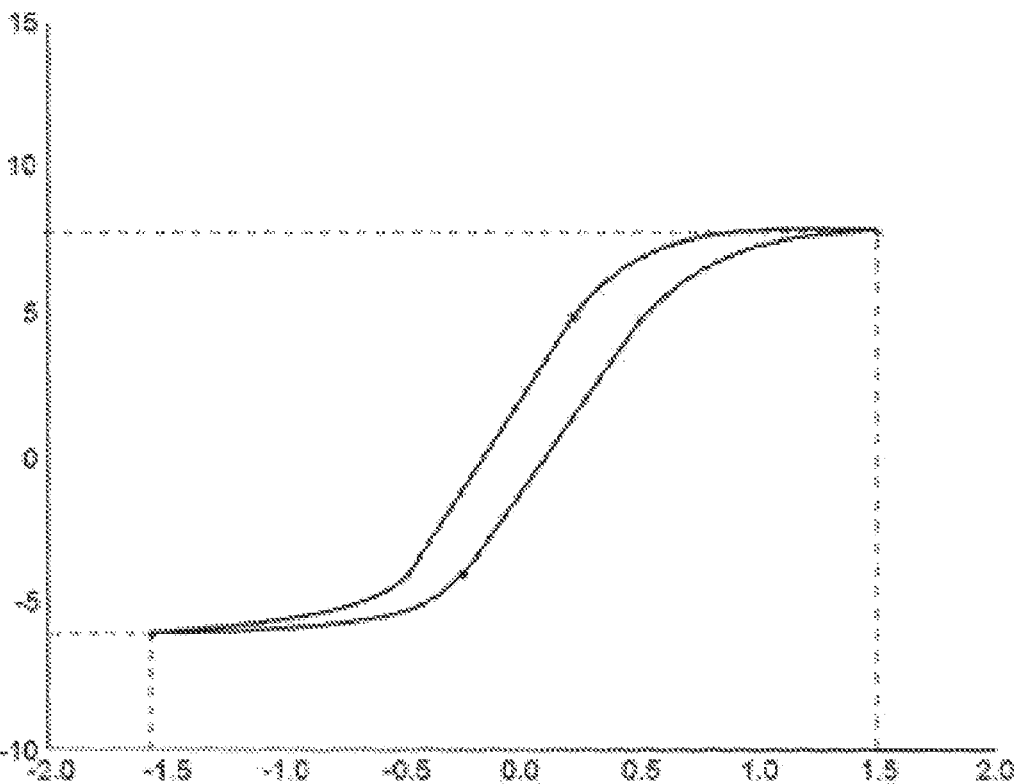
Figure 23:
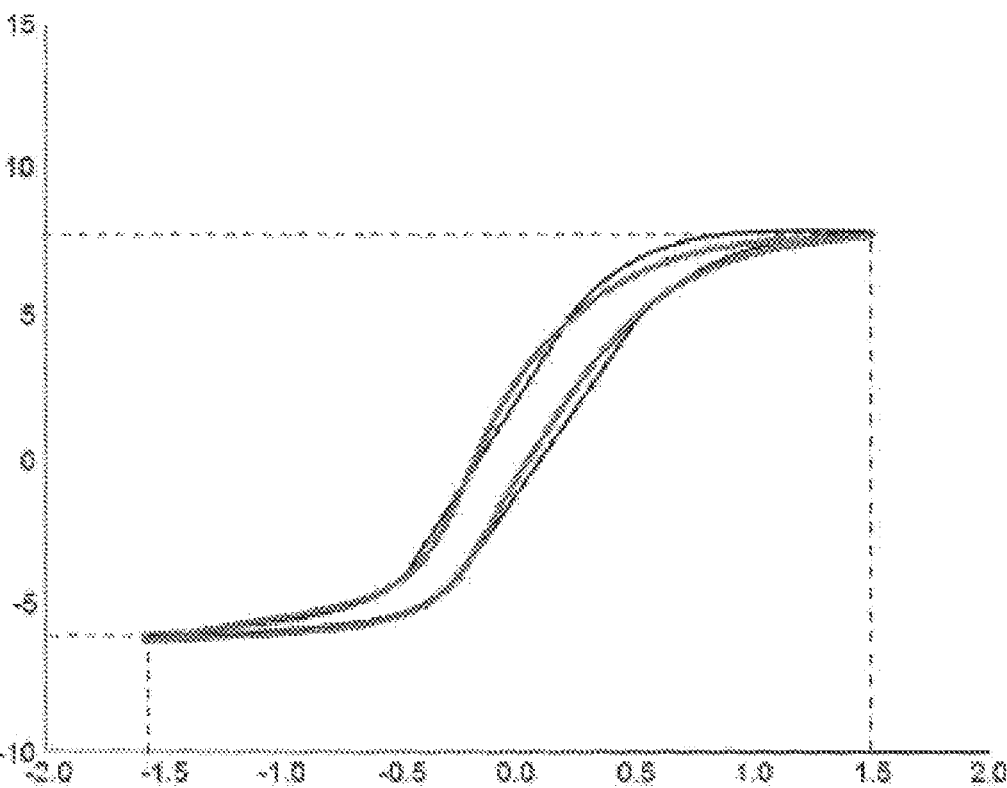
Figure 24:
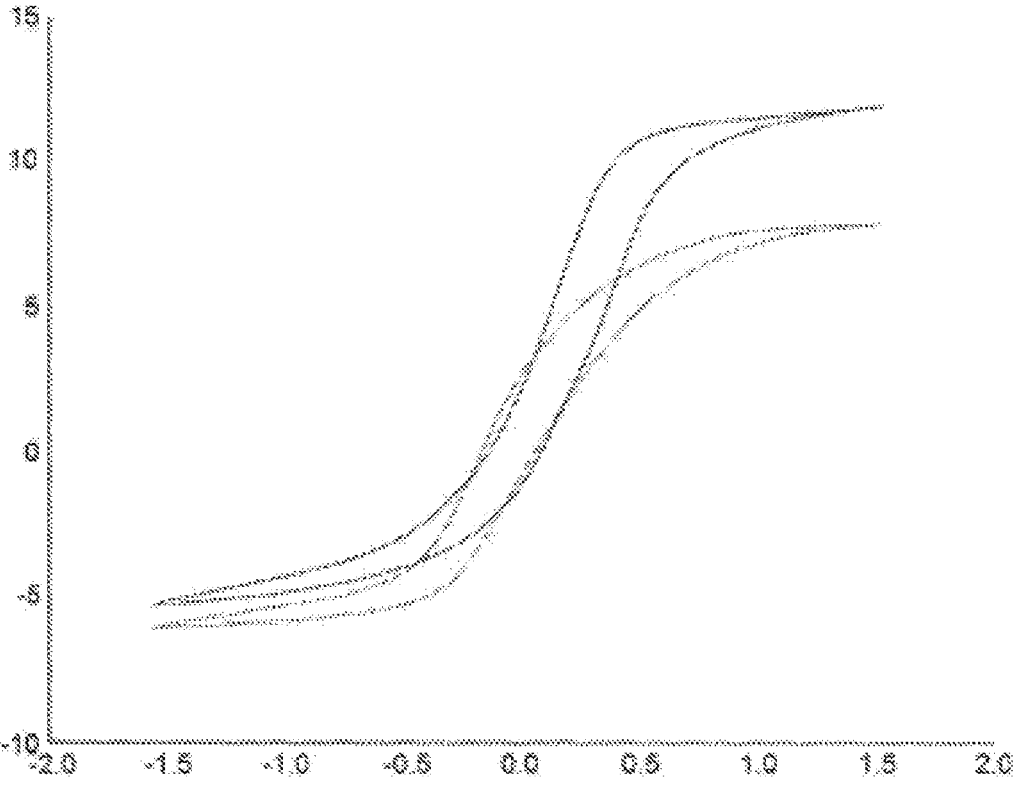

FIG. 20 illustrates the next step of establishing the high flexibility zone unloading knees. These may be established by, for example, using a percentage of the full range of motion (e.g., approximately two thirds of the full range of motion). Once the loading and unloading knees have been established, the full high flexibility zone may be established as the zone between the respective loading and unloading knees, as illustrated in FIG. 21. Then, the remainder of the curve may be established by connecting the full range of motion points to the high flexibility zone using any desired method, such as fitting Botzmann curve, a DIP Botzmann curve, or simply a freehand curve. FIG. 23 illustrates how in vitro results may compare to the modeled and expected results. Additionally, FIG. 24 illustrates that the method functions regardless of the range of motion initially determined.

Once the desired spinal kinetic curve has been established, the spinal implant can be assembled and/or modified to provide the desired spinal kinetic curve. Specifically, the flexures can be modified, formed, and/or shaped to provide a desired stiffness and/or range of motion. The thickness, width, length and/or shape of the flexures of the present total disc replacement can then each be specifically selected to provide the desired metrics to the spinal segment after implantation of the spinal implant.

While FIGS. 15-24 illustrate one method for establishing the parameters that should be used in tailoring a spinal implant as discussed above, it will be recognized that the method can be varied while still achieving desired results. Specifically, other constants could be used. Additionally, instead of X-ray imaging, a series of images or video could be used to determine the appropriate physical parameters. Still further, a machine could be used to manipulate the spine so as to reduce variability. In some cases, one or more of the determined points used to generate the curve may be eliminated. External or internal markers attached to the spinal processes may also be used instead of images. The range of motion of the spinal segment of interest may be used, or the range or motion for the adjacent spinal segments may be used if it is felt that the degeneration of the spinal segment of interest has impacted the range of motion of the spinal segment of interest.

It should also be appreciated that any features of the spinal implant may be modified to comport with the anatomy of the patient of interest as well as the anatomy of the spinal segment of interest. Specifically, while illustrative embodiments of the spinal implant have been illustrated in the Figures, it should be appreciated that the size and shape of the spinal implant, as well as the curvature of the various surfaces of the spinal implant may be varied to fit the anatomy of the individual patient and/or spinal segment. For instance, a spinal implant for a large man may be larger than a spinal implant for a petite woman. Similarly, a spinal implant intended for a cervical spine segment will be smaller than a spinal implant intended for a lumbar spine segment.

Additionally, as mentioned above, the spinal implant may be tailored with respect to an anticipated surgical approach. For example, if an anterior surgical approach is to be used, it may be anticipated that the anterior longitudinal ligament will be excised, and the stiffness of the spinal implant may be tailored to compensate for the loss of stability incurred due to the loss of the ligament in the surgery. In contrast, if a direct lateral approach, passing through the psoas muscle without impacting ligaments or causing stability losses in the spinal segment, and the spinal implant in such a case can be tailored with an appropriate stiffness accordingly.

Embodiments of the spinal implant disclosed herein provide additional benefits, such as:

Kinetics similar to a healthy spine: Embodiments of the spinal implant provide relative motion to vertebra in the three axes discussed above regarding FIG. 5 similar to that of a healthy spine. One result of this benefit is that the patient's muscles and ligaments do not have to compensate for an unnatural motion of the spinal implant, unlike the case with prior art devices. In other words, the spinal implant provides more natural motion, which would encourage patients to move more with less attendant pain as their muscles would not be compensating or overworking for a prior art spinal implant that does not provide such natural motion around all three axes.

Kinematics similar to a healthy spine: Related to the kinetics are the natural kinematics of embodiments of the spinal implants. As discussed above, the centers-of-rotation for flexion-extension, lateral extension/bending, and axial rotation, are each located in different places. Prior art devices cannot accommodate these separate centers-of-rotation around more than one axis, if even that; nor can they provide for the instantaneous or near instantaneous change in the location of the centers-of-motion as a spinal segment moves; nor can they provide for motion approximate the motion of a natural helical axis. Stated differently, the center-of-rotation of prior art devices is often in a different location than the natural center-of-rotation of the spine for a given movement. To compensate, patients with prior art devices suffered strain upon the spinal cord and peripheral nerves, muscle strain caused by the muscles overworking and compensating for the two different centers-of-rotation (that of the prior art device and that of the spine), ligament strain, and, consequently, pain. In contrast, embodiments of the present spinal implant provide centers-of-rotation in each of the three axes that are the same, or nearly the same, as a patient's natural centers-of-rotation for the spine. Thus, patients typically have less pain and, consequently, greater movement, to the benefit of the discs and the spine in general.

Adjust to the individual spine: As noted, embodiments of the spinal implant can be designed and/or selected preoperatively for an individual patient in order to provide implants that restore the diseased spine to near healthy function. That is, the particular geometry of the spinal implant and its components can be individually tailored to a particular patient and the particular location within the patient's spine at which the spinal implant is to be implanted.

Thus, disclosed above, in addition to the embodiments of the spinal implant are methods of treating a spine with a spinal implant, such as an intervertebral disc prosthesis, configured to provide motion in three axes and that provides kinetics and kinematics similar to that of a functional spine, as well as other methods that will be recognized by one of skill in the art.

As alluded to above, embodiments of methods of using the spinal implant are disclosed. While the spinal implants disclosed herein can be positioned within a spinal segment by using an anterior, posterior, or lateral approach in the patient, a preferred method is to use a posterior approach. Further, it is preferred that a minimally invasive procedure be used, such as by laparoscopy in which only one or a few, small incisions are made and the surgery is conducted with laparoscopic tools. The methods include making an incision; providing an embodiment of the spinal implant disclosed herein; positioning the spinal implant between a first vertebra and a second vertebra; and coupling the spinal implant to at least the first vertebra. Securing the spinal implant to the vertebrae may be done by applying straps, applying biocompatible adhesives, installing pedicle screws, and the like, as known in the art.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A method of tailoring a spinal implant to correspond to a specific patient's needs, the method comprising:
    pre-operatively evaluating information regarding a patient to determine a desired spinal segment stiffness response, comprising:
determining a first range of motion for a target spinal segment, the first range of motion for the target spinal segment comprising at least two of:
        a flexion/extension component;
        a lateral bending component;
an axial rotation component; and
        a compression component;

18 wherein the determining the first range of motion for the target spinal segment comprises:
        manipulating the target spinal segment within the first range of motion under a load; and
        capturing and reviewing images of the target spinal segment as manipulated along the at least two of the flexion/extension component, the lateral bending component, the axial rotation component, and the compression component;
    determining a hysteresis curve for the target spinal segment based on the first range of motion as determined from the images; and
    modifying one or more flexures of the spinal implant to cause the spinal implant to correspond with the first range of motion of the target spinal segment to provide the desired spinal segment stiffness response.

2. The method of claim 1, wherein the first range of motion for the target spinal segment comprises each of the flexion/extension component, the lateral bending component, the axial rotation component, and the compression component.

3. The method of claim 1, wherein the capturing and reviewing images comprises capturing and reviewing X-ray images as the patient manipulates a spine of the patient within the first range of motion.

4. The method of claim 1, wherein the first range of motion is determined from imaging of markers attached at the target spinal segment while under the load.

5. The method of claim 1, wherein the first range of motion is determined from a series of images or video of the target spinal segment under the load.

6. The method of claim 1, wherein the determining the hysteresis curve for the target spinal segment further comprises fitting at least one of a Boltzmann curve, a DIP Boltzmann curve, and a freehand curve to data points determined from the images.

7. A method of tailoring a spinal implant to correspond to a specific patient's needs, the method comprising:
    pre-operatively evaluating information regarding a patient to determine a desired spinal segment response, comprising:
        determining a first range of motion for a target spinal segment, the first range of motion for the target spinal segment comprising at least two of:
        a flexion/extension component;
        a lateral bending component;
        an axial rotation component; and
        a compression component;
    wherein the determining the first range of motion for the target spinal segment comprises:
        manipulating the target spinal segment within the first range of motion under a first load; and
        capturing and reviewing images of the target spinal segment as manipulated along the at least two of the flexion/extension component, the lateral bending component, the axial rotation component, and the compression component;
    determining a hysteresis curve for the target spinal segment based on the first range of motion as determined from the images; and
    modifying one or more features of the spinal implant to provide the desired spinal segment response.

8. The method of claim 7, wherein the method further comprises manipulating a second spinal segment adjacent the target spinal segment within a second range of motion under a second load, and capturing and reviewing images of the second spinal segment as manipulated within the second range of motion.

9. The method of claim 7, wherein the method further comprises determining a high-flexibility zone (HFZ) range of motion using a calculation of a percentage of the first range of motion, and wherein the determining the hysteresis curve for the target spinal segment further comprises taking into account the HFZ range of motion as determined from the calculation.

10. The method of claim 7, wherein the method further comprises:

determining a high-flexibility zone (HFZ) range of motion by:

manipulating the target spinal segment within the first range of motion under a second load that is less than the first load; and capturing and reviewing a second set of images of the target spinal segment as manipulated within the first range of motion under the second load, wherein the determining the hysteresis curve for the target spinal segment further comprises taking into account the HFZ range of motion as determined from the second set of images.

11. The method of claim 7, wherein the modifying one or more features of the spinal implant comprises modifying at least one of a thickness, a width, a length, and a shape of one or more flexures of the spinal implant.

12. The method of claim 7, wherein the first range of motion for the target spinal segment comprises at least three of the flexion/extension component, the lateral bending component, the axial rotation component, and the compression component.

13. The method of claim 7, wherein the first range of motion for the target spinal segment comprises each of the flexion/extension component, the lateral bending component, the axial rotation component, and the compression component.

14. The method of claim 7, wherein the determining the hysteresis curve for the target spinal segment further comprises fitting at least one of a Boltzmann curve, a DIP Boltzmann curve, and a freehand curve to data points determined from the images.

15. A method of tailoring a spinal implant to correspond to a specific patient's needs, the method comprising:

pre-operatively evaluating information regarding a patient to determine a desired spinal segment stiffness response, comprising:

determining a first range of motion for a target spinal segment, the first range of motion for the target spinal segment comprising:

a flexion/extension component;

a lateral bending component;

an axial rotation component; and a compression component;

wherein the determining the first range of motion for the target spinal segment comprises:

manipulating the target spinal segment within the first range of motion under a first load; and capturing and reviewing images of the target spinal segment as manipulated along each of the flexion/extension component, the lateral bending component, the axial rotation component, and the compression component;

determining a hysteresis curve for the target spinal segment based on the first range of motion as determined from the images; and modifying one or more features of the spinal implant to cause the spinal implant to correspond with the first range of motion of the target spinal segment to provide the desired spinal segment stiffness response.

16. The method of claim 15, wherein the method further comprises determining a high-flexibility zone (HFZ) range of motion using a calculation of a percentage of the first range of motion, and wherein the determining the hysteresis curve for the target spinal segment further comprises taking into account the HFZ range of motion as determined from the calculation.

17. The method of claim 16, wherein the determining the hysteresis curve for the target spinal segment further comprises fitting at least one of a Boltzmann curve, a DIP Boltzmann curve, and a freehand curve to data points determined from the images and the calculation.

18. The method of claim 15, wherein the method further comprises:

determining a high-flexibility zone (HFZ) range of motion by:

manipulating the target spinal segment within the first range of motion under a second load that is less than the first load; and capturing and reviewing a second set of images of the target spinal segment as manipulated within the first range of motion, wherein the determining the hysteresis curve for the target spinal segment further comprises taking into account the HFZ range of motion as determined from the second set of images.

19. The method of claim 18, wherein the determining the hysteresis curve for the target spinal segment further comprises fitting at least one of a Boltzmann curve, a DIP Boltzmann curve, and a freehand curve to data points determined from the images and the second set of images.

20. The method of claim 15, wherein the desired spinal segment stiffness response comprises an energy curve corresponding to the hysteresis curve.

21. The method of claim 15, wherein the modifying one or more features of the spinal implant comprises modifying at least one of a thickness, a width, a length, and a shape of one or more flexures.

22. The method of claim 15, wherein the determining the hysteresis curve for the target spinal segment further comprises fitting at least one of a Boltzmann curve, a DIP Boltzmann curve, and a freehand curve to data points determined from the images.

* * * * *